(12) United States Patent
Pruckner et al.

(10) Patent No.: US 9,072,565 B2
(45) Date of Patent: Jul. 7, 2015

(54) MEDICAL TREATMENT DEVICE

(75) Inventors: Christian Pruckner, Vienna (AT);
Roland Sevcik, Bad Reichenhall (DE)

(73) Assignee: W & H Dentalwerk Burmoos GmbH, Burmoos (AT)

( * ) Notice: Subject to any disclaimer, the term of this patent is extended or adjusted under 35 U.S.C. 154(b) by 830 days.

(21) Appl. No.: 13/186,025

(22) Filed: Jul. 19, 2011

(65) Prior Publication Data

US 2012/0022393 A1 Jan. 26, 2012

(30) Foreign Application Priority Data

Jul. 22, 2010 (EP) .................................. 10 170 440
Apr. 21, 2011 (EP) .................................. 11 163 340

(51) Int. Cl.
*A61C 19/00* (2006.01)
*A61C 1/00* (2006.01)

(52) U.S. Cl.
CPC .................................. *A61C 1/0015* (2013.01)

(58) Field of Classification Search
CPC .... A61B 5/053; A61B 5/0537; A61B 5/0538; A61B 5/01; A61B 5/0531; A61B 5/0205; A61B 5/0536; A61B 5/4836; A61B 5/7285; A61B 5/74; A61B 5/7405; A61B 5/7425; A61B 6/482; A61B 6/504
USPC ............. 600/547, 536, 506, 324; 433/25, 27; 601/2
See application file for complete search history.

(56) References Cited

U.S. PATENT DOCUMENTS 3,433,226 A * 3/1969 Boyd ............................ 606/159
3,636,943 A * 1/1972 Balamuth ........................ 601/2
3,657,056 A * 4/1972 Winston et al. ............ 156/580.2

(Continued)

FOREIGN PATENT DOCUMENTS

EP 0 394 583 A2 10/1990

OTHER PUBLICATIONS

Extended European Search Report dated Dec. 23, 2010 issued in the priority application No. EP 10 17 0440.1.

*Primary Examiner* — Max Hindenburg
*Assistant Examiner* — Jonathan M Foreman
(74) *Attorney, Agent, or Firm* — Wood, Phillips, Katz, Clark & Mortimer

(57) ABSTRACT

A medical treatment device comprises a sensor to detect operating states of the medical treatment device, wherein the sensor comprises a first electrode, a second electrode and impedance means. The first electrode is arranged between a current path input and a current path output, wherein an electric input signal for powering the medical treatment device is applicable to the current path input, and the current path output is configured to couple to a load of the medical treatment device. The second electrode is separated from the first electrode by a first dielectric material, the second electrode comprising a first signal terminal for obtaining a first sensor signal. The impedance means are separated from the first electrode by a second dielectric material and comprise a second signal terminal for obtaining a second sensor signal. The first electrode comprises a cross section perpendicular to the direction of propagation of the electric input signal such that the first electrode and the second electrode are coupled to provide a capacitance as first sensor signal, and wherein the impedance means are formed as a structured electrode such that the first electrode and the impedance means are coupled to provide an impedance as second sensor signal.

22 Claims, 26 Drawing Sheets

(56) References Cited

U.S. PATENT DOCUMENTS

| | | | |
|---|---|---|---|
| 3,819,961 A * | 6/1974 | Bourgeois et al. | 310/316.01 |
| 4,012,647 A * | 3/1977 | Balamuth et al. | 310/317 |
| 4,168,447 A | 9/1979 | Bussiere et al. | |
| 5,140,231 A * | 8/1992 | Kashiyama | 318/116 |
| 5,198,713 A | 3/1993 | Suzuta | |
| 5,359,268 A * | 10/1994 | Kashiyama | 318/116 |
| 5,376,855 A * | 12/1994 | Suganuma | 310/316.02 |
| 5,394,047 A * | 2/1995 | Scharlack et al. | 310/316.01 |
| 5,477,100 A | 12/1995 | Kataoka | |
| 5,612,598 A * | 3/1997 | Fukui et al. | 318/116 |
| 5,759,159 A * | 6/1998 | Masreliez | 600/547 |
| 6,083,191 A * | 7/2000 | Rose | 604/22 |
| 6,292,690 B1 * | 9/2001 | Petrucelli et al. | 600/547 |
| 6,997,883 B1 * | 2/2006 | Hahn | 600/560 |
| 7,427,265 B1 * | 9/2008 | Keilman et al. | 600/300 |
| 7,494,468 B2 * | 2/2009 | Rabiner et al. | 600/459 |
| 2001/0039389 A1 * | 11/2001 | Sakurai et al. | 601/2 |
| 2007/0085611 A1 | 4/2007 | Gerry et al. | |

* cited by examiner

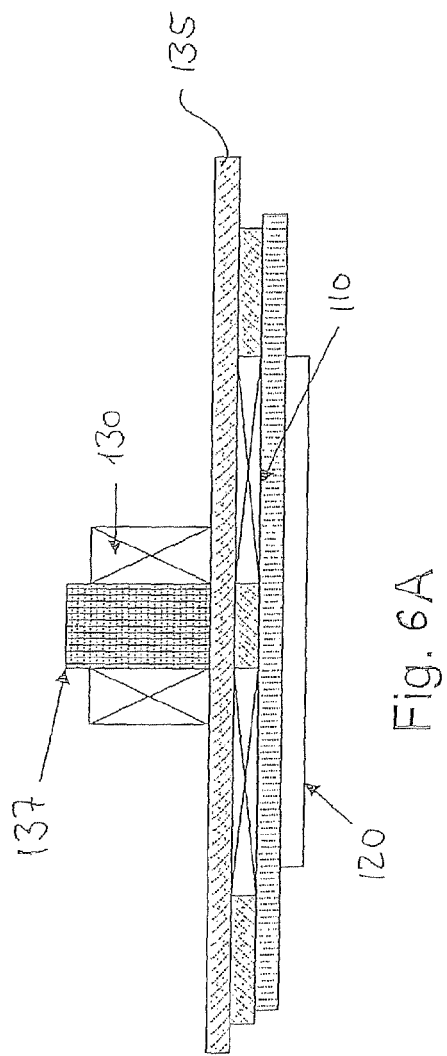
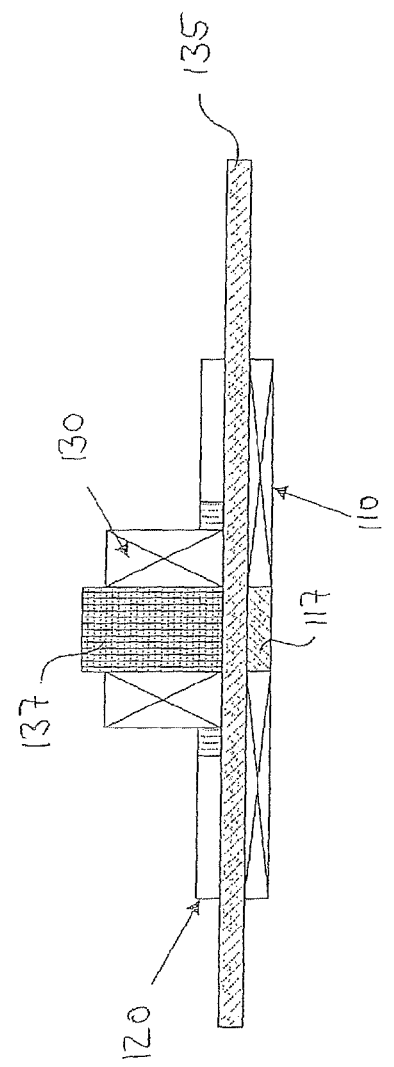

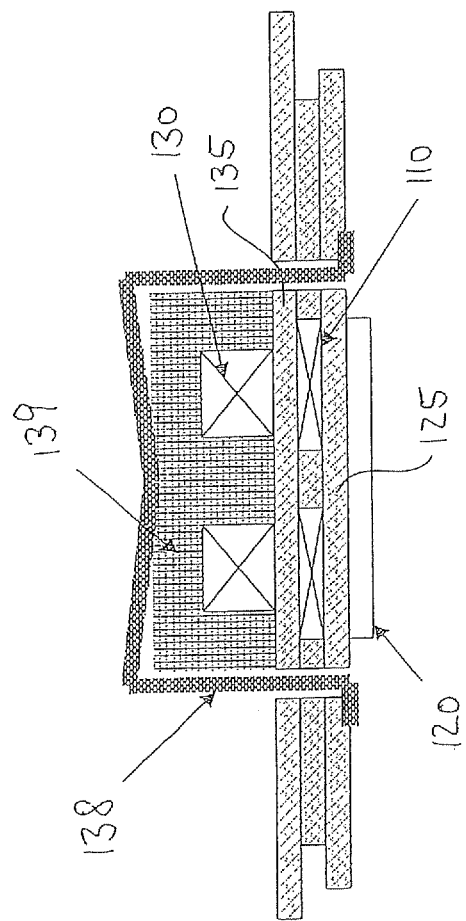

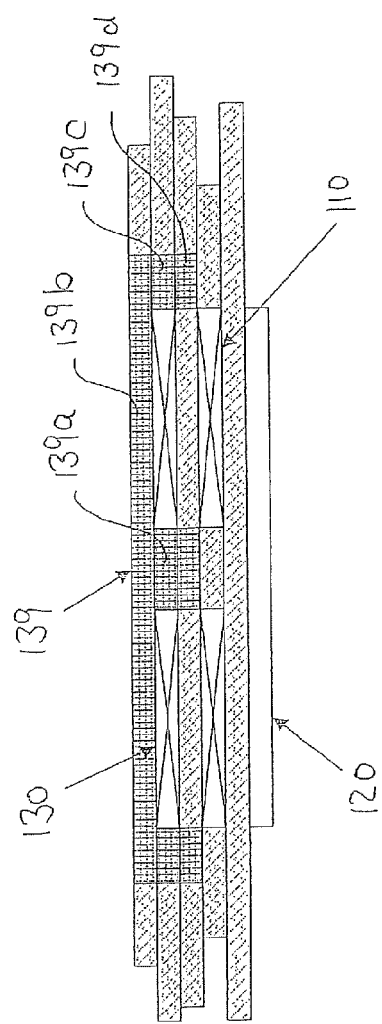
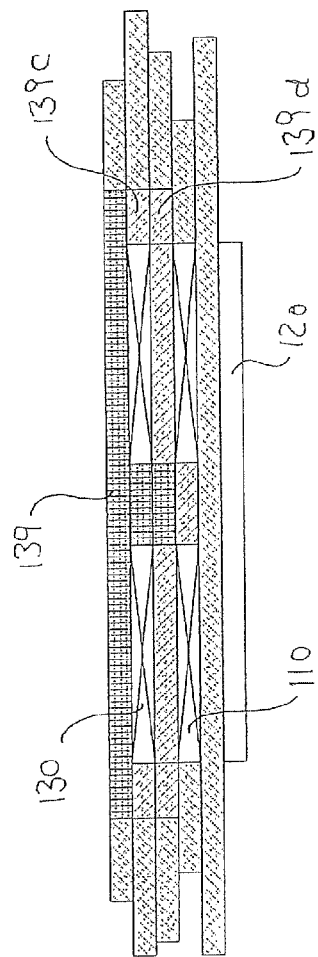
Fig. 10A
Fig. 10B

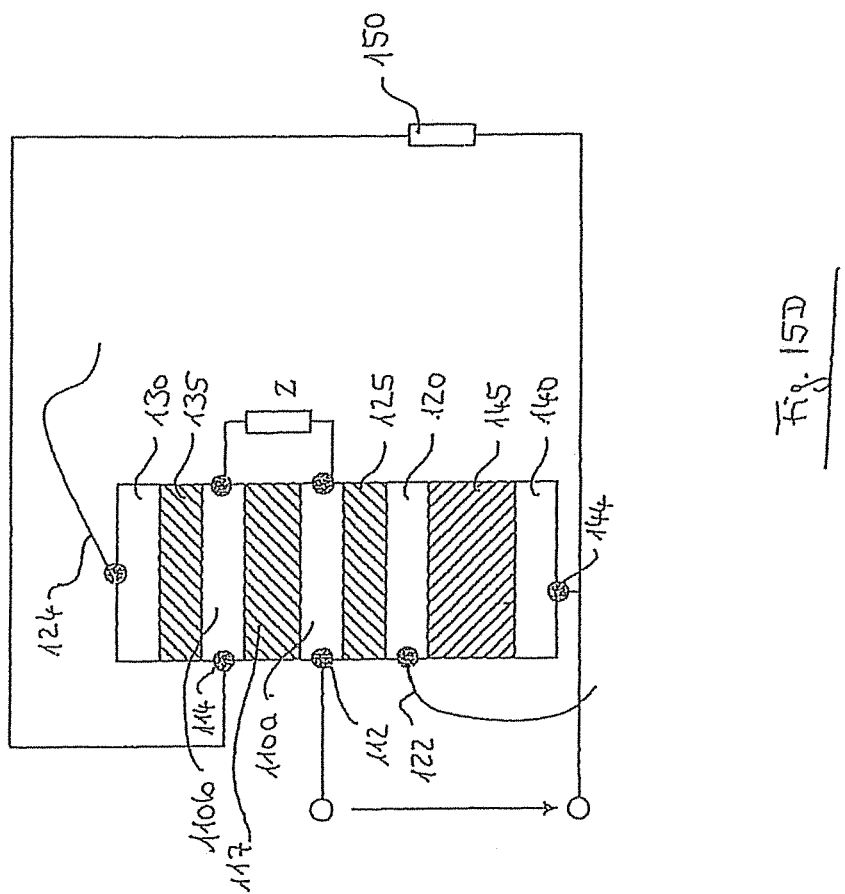

MEDICAL TREATMENT DEVICE

The present invention relates to a medical treatment device having a sensor, and in particular to a powered medical, in particular dento-medical, instrument, in particular having a hand-piece, which comprises a combined capacitive-inductive or a capacitive-capacitive sensor.

BACKGROUND OF THE INVENTION

Medical, in particular dento-medical, powered instruments often require that the operating state should be continuously monitored to control or adjust the output of an electric drive or of another electric component on the basis of these measurements, for example. This is very important in medical instruments such as a powered scaling hand-piece (scaler hand-piece), as these instruments comprise, for example, an electric vibration generator (e. g. a piezoelectric motor). In the ideal case, the piezoelectric motor (vibration generator with piezoelectric elements) operates at a resonance frequency which is to be provided by the applied electric signal for an optimum operation. In this case, the problem occurs that the resonance frequency depends, for example, on the load and may therefore continuously change during use.

Patent specification U.S. Pat. No. 6,976,843 B2 discloses a dental treatment device allowing a plurality of hand-pieces operating at different resonance frequencies to be operated by means of an ultrasonic generator. The adjustment to the resonance frequencies is done through passive elements such as capacitors, which, together with the hand-piece, are connected to the ultrasonic generator. The passive elements have the effect that the resonance frequency provided by the ultrasonic generator for the respective hand-piece is appropriately adapted to the hand-piece.

Patent specification No. EP 1 191 895 B1 discloses a control device for a dental ultrasonic hand-piece, which is configured to electrically compensate for a phase shift occurring between the voltage and the supplied current due to an intrinsic capacitance of the ultrasonic generator. To that end, a secondary circuit is arranged in addition to the primary circuit, which is connected to the primary circuit through a converter and comprises a variable inductance and a variable capacitance on the secondary side. If the hand-piece does not operate at the resonance frequency due to loading, for example, and the current and voltage signals exhibit a relative phase shift, the inductance is changed on the secondary side of the converter so that the phase of the current on the primary side will also shift and in turn the hand-piece is allowed to be brought into resonance.

The patent specification mentioned first only allows an adjustment of the resonance frequency by means of one or more passive elements and hence only an adjustment to discrete resonance frequencies is possible, whereas the second patent specification utilizes a secondary circuit in order to first sense a measurand such as a relative phase shift between the current signal and the voltage signal and then to compensate for the determined phase shift by means of continuously changing the inductance on the secondary side.

The disadvantage of these two approaches is that it is impossible to detect the operating state in a flexible and low-loss manner and to make an adjustment on the basis of this detection, which continuously allows a resonant operation. Another disadvantage is that the control is accompanied with losses due to additional inductances/capacitances, which are not acceptable for many applications.

Therefore, an improved medical treatment device and an improved control of the medical treatment device are demanded, which in particular allows to continuously detect and control the operating state of the treatment device through simplest possible means and at the lowest possible loss.

SUMMARY OF THE INVENTION

Embodiments of the present invention include a medical treatment device having a sensor to detect operating states of the medical treatment device, the sensor including the following features: a first electrode arranged between a current path input and a current path output, wherein an electric input signal for powering the medical treatment device is applicable to the current path input, and the current path output is configured to couple to a load of the medical treatment device. The sensor further includes a second electrode which is electrically isolated from the first electrode by a first dielectric material, the second electrode including a first signal terminal for receiving a first sensor signal (or sense signal). The sensor also includes impedance means which are isolated from the first electrode by a second dielectric material, the impedance means including a second signal terminal for picking off a second sensor signal. In this sensor, the first electrode is configured to have a cross section perpendicular to the direction of propagation of the electric input signal in such a way that the first electrode and the second electrode couple to provide an impedance (e.g. a capacitance or inductance) as a first measuring signal (sensor signal). The impedance means are formed as a structural electrode so that the first electrode and the impedance means couple to provide a further impedance (e.g. a capacitance or inductance) as a second measuring signal (sensor signal).

Other embodiments additionally include an evaluating unit (processing unit) to receive or detect the second sensor signal (e. g. a capacitive and/or inductive measuring signal) and to determine from this signal a current signal and/or a voltage signal and/or a frequency for the electric input signal and/or to determine their relative phase to each other. The current signal/voltage signal may include, for example, the amplitude, the frequency and/or the phase relationship of the intensity of current/voltage (e. g. the current intensity I as a function of the amplitude A, of the frequency f and of the phase $\phi$, or analogously for the voltage). The current and voltage signals determined in such a way and the relative phase relationship may further be provided to a power supply device (power unit) serving for the power supply of the treatment device to change, for example, the relative phase relationship between the current signal and the voltage signal and/or the frequency of the electric input signal. The change may be effected, for example, through a control signal which is output by the evaluating unit and is supplied to the power supply device. This makes it possible to have a closed control loop which continuously monitors the current and voltage signals and changes them appropriately. The power supply device generates the electric input signal, for example. The control signal is configured to cause the power supply device to change the electric input signal in order to change or to eliminate a phase shift and/or a frequency, for example, or to restore a resonance of the medical treatment device (resonant operation). It is, therefore, an advantage of the evaluating unit that the operating state of the treatment device may be adjusted as requested (e. g. resonant operation) by simple means while the load changes continuously.

In further embodiments, the impedance means are configured as a capacitive or inductive sensor or as a combination of capacitive and/or inductive sensors.

In embodiments of the present invention, contact electrodes are therefore arranged along the current path for powering the medical treatment device by means of the current path input and the current path output in such a way that a first, a second and a third capacitor will form, the first and the third capacitor being connected in series between the current path input and a ground potential and the second capacitor being connected between the current path input and a reference potential. In this way, a first measuring signal may be picked off between the first and the third capacitor and a second measuring signal may be picked off at the output of the second capacitor. According to the invention, the first and the third capacitor share a common contact electrode extending between the current path input and the current path output. The electric input signal for powering the medical treatment device may be applied to the current path input and a load of the medical treatment device may be applied to the current path output. The load includes, for example, a piezoelectric motor or similar current consumers.

The first capacitor is formed by a first and a second contact electrode. The first contact electrode is arranged between a current path input and a current path output, wherein an electric input signal for powering the medical treatment device is applicable to the current path input and the current path output is adapted to couple to a load of the medical treatment device. The second contact electrode is isolated from the first contact electrode by a first dielectric material, and the second capacitor is formed by a first contact electrode and a third contact electrode, which is isolated from the first contact electrode by a second dielectric material. The second contact electrode includes a first measuring signal output (first signal terminal) for picking off the first (capacitive) measuring signal and the third contact electrode includes a second measuring signal output (second signal terminal) for picking off the second (capacitive) measuring signal. Finally, a fourth contact electrode having a reference terminal for coupling to the ground potential is configured in such a way that the fourth contact electrode is isolated from the second contact electrode by a third dielectric material.

In this way, a capacitive sensor for a medical treatment device is provided, which allows, for example, to determine or to detect current and voltage simultaneously and with high fidelity. In this case, it is possible to determine by means of the sensor only the current or only the voltage and to provide it to further processing. The detection with high fidelity refers, for example, to the variation in the amplitude or phase or voltage or current with time.

In further embodiments, the evaluating unit is optionally configured to determine a power requirement of the medical treatment device from the capacitive and the inductive measuring signal or to change it through the control signal. The capacitive and the inductive measuring signal may, for example, be picked off in terms of a first and a second reference potential, the first and the second reference potential being selected in such a way that they are equal to or different from each other and, in addition, in such a way that they are equal to or different from the ground potential. By this, a galvanic isolation is achieved. It is an advantage of the different reference potentials that they may be matched to the current signal strength.

In further embodiments, the impedance means are configured as an inductive sensor. In these embodiments, the sensor includes a first planar electrode and a second planar electrode. The first planar electrode is arranged between a current path input and a current path output, an electric input signal for supplying the medical treatment device being applicable to the current path input and a load of the medical treatment device being applicable to the current path output. The second planar electrode is isolated from the first planar electrode by a first dielectric material and comprises a first measuring signal terminal for picking off a capacitive measuring signal (sensor signal). In these embodiments, the sensor further comprises an induction element.

In addition, the first planar electrode may be configured as a planar coil. The induction element is isolated from the first planar electrode by a second dielectric material and is arranged between a second measuring signal terminal and a third measuring signal terminal. An inductive measuring signal may be picked off between the second measuring signal terminal and the third measuring signal terminal. The first planar electrode comprises a cross section perpendicular to the direction of propagation of the electric input signal so that the first planar electrode and the second planar electrode may be coupled capacitively and the first planar electrode and the induction element may be coupled inductively.

Here, capacitive/inductive coupling means, for example, that the coupled components are interconnected in such a way that the coupling may be represented in an electric equivalent circuit diagram as a capacitor or as a coil or as a transformer. This may be achieved, for example, by an elongated cross section of the first planar electrode along the planar direction of the planar electrode/planar coil so that one of the two dimensions is longer and extends in the (planar) plane of the planar electrode. This allows a very compact design so that the sensor may be arranged in different positions in the treatment device. In the course of increasing miniaturization, this is a major advantage.

In further embodiments, the induction element comprises a further planar coil (second coil) having a larger winding number than the planar coil (first planar coil). This makes it possible to transform the inductive measuring signal appropriately so that, for example, the inductive measuring signal is transformed into another voltage range and hence the signal detection or signal separation may be improved.

In further embodiments, the first planar electrode wound into the planar coil is configured so that it specifically comprises a rectangular cross section (for example, each individual turn), the longer side of the rectangle being aligned, for example, in parallel to the second planar electrode. In this case, the cross section refers to, for example, an intersecting plane perpendicular to the direction of current of the measuring signals or of the electric input signal of the medical treatment device. The second planar electrode may be designed as a planar capacitor plate, for example, so that the longer side of the rectangle of the first planar electrode is arranged in parallel to the capacitor plate. This has the effect that the capacitive coupling between the first planar electrode and the second planar electrode is increased, as the overlapping surface area of the opposing capacitor electrodes (first and second planar electrodes) is crucial to the capacitance of the capacitive coupling in addition to the distance. This surface area may be maximized by providing the first planar electrode with a cross section which is elongated as possible. This may be achieved by, for example, minimizing the dimension in the direction perpendicular to the second planar electrode (=direction of the normal), while keeping a constant cross-sectional area to be used by the current density.

In further embodiments, the medical treatment device having the described sensor comprises a hand-piece having, for example, a piezoelectric motor or an electric motor as a load, which is designed for dental treatment and specifically for scaling, for example. Alternatively, the sensor is arranged in a control device for the hand-piece having a piezoelectric motor. Optionally, the described sensor may be also arranged in a power supply line between the control device and the hand-piece.

In this case, too, it is optionally possible to configure the sensor of the medical treatment device as a printed circuit board on which the planar electrodes and the dielectric layers (dielectric materials) are stacked as layers on top of one another, or to configure it by the fact that the printed circuit board itself is one of the dielectric layers (i. e. the first or the second dielectric material). Also possible is a coaxial arrangement in which the respective planar electrodes are arranged to each other in the form of a (semi)cylinder at different distances in the radial direction and are isolated from each other by dielectric layers so that the dielectric layers may also be arranged coaxially to each other. The advantages of these embodiments are that simple means (such as printed circuit boards) may be utilized and that positioning (e. g. in the case of a coaxial arrangement within a power supply line) can be done in a flexible manner.

In a further embodiment of the present invention, a medical treatment device includes a sensor for detecting operating states of the medical treatment device, wherein the sensor now comprises only the following features: a first planar electrode for powering the medical treatment device, which is arranged between a current path input and a current path output, wherein an electric input signal is applicable to the current path input (i.e. it is configured to couple to a power supply) and the current path output is configured to couple to a load of the medical treatment device; and a second planar electrode for receiving a capacitive sensor signal, wherein the second planar electrode includes a signal terminal (sensor terminal) for the capacitive sensor signal. Finally, the sensor includes a dielectric material for electrically isolating the first and the second planar electrode.

Embodiments also include a method for controlling an input signal for powering a load of the described medical treatment device, the method comprising: detecting the first sensor signal; detecting the second sensor signal; determining the control signal based on the first control signal and the second sensor signal; and providing the control signal to a power supply unit in such a way that the control signal changes the electric input signal. In the method, the control signal may optionally be provided in such a way that the phase shift between the current signal and the voltage signal is reduced to provide a resonant operation of the load. In addition, the control signal in the method may be configured to change a real power consumed by the load, in such a way that the efficiency of the treatment device increases. As a result, the method utilizes, for example, the medical treatment device as described above. Other features described by means of the device are also utilized in the method in further embodiments.

Embodiments of the present invention have a number of advantages over the prior art. For example, the sensor is very small and compact and the capacitive and inductive coupling does not generate additional load on the medical treatment device. The sensor measures, for example, just where the load couples or where a high current and/or voltage apply (e. g. their maximum values in the treatment device). As a result, a direct feedback to the power supply unit is possible (which in turn changes the supply voltage/current/frequency appropriately) without needing additional variable inductances/capacitances, which results in a decrease in losses. The advantageous low physical size is also achieved by the fact that the first planar electrode acts both as an electrode for the capacitive measuring signal and an electrode (coil) for the inductive measuring signal.

Other advantages are that the values detected by the sensor may be used to derive or to calculate the impedance, real power, reactive power and other parameters by means of appropriate circuits or control devices, for example, and to use them for control or adjustment. The values measured by the sensor may be used to control and to adjust the output of electrically operated scaler hand-pieces or piezoelectric scalers and/or to find, to maintain or to display the resonance point (or resonance frequency) for the tool (scaler tip) connected to the scaler.

BRIEF DESCRIPTION OF THE DRAWINGS

The invention will be described hereafter in further detail with reference to the accompanying drawings, in which:

FIGS. 6A, B illustrate side views of another embodiment using soft magnetic coil cores;

FIG. 9 illustrates a side view of an embodiment in which the induction element is embedded in a soft magnetic coil core;

FIGS. 10A, B illustrate side views of multilayer PCBs having an embedded ferrite material according to other embodiments;

FIGS. 15A-E illustrate perspective views of the medical treatment device as well as further embodiments of the present invention;

FIG. 17 illustrates an idealized view of a phase shift between a current measuring signal and a voltage measuring signal, which is to be compensated for;

DETAILED DESCRIPTION

Figure 1:
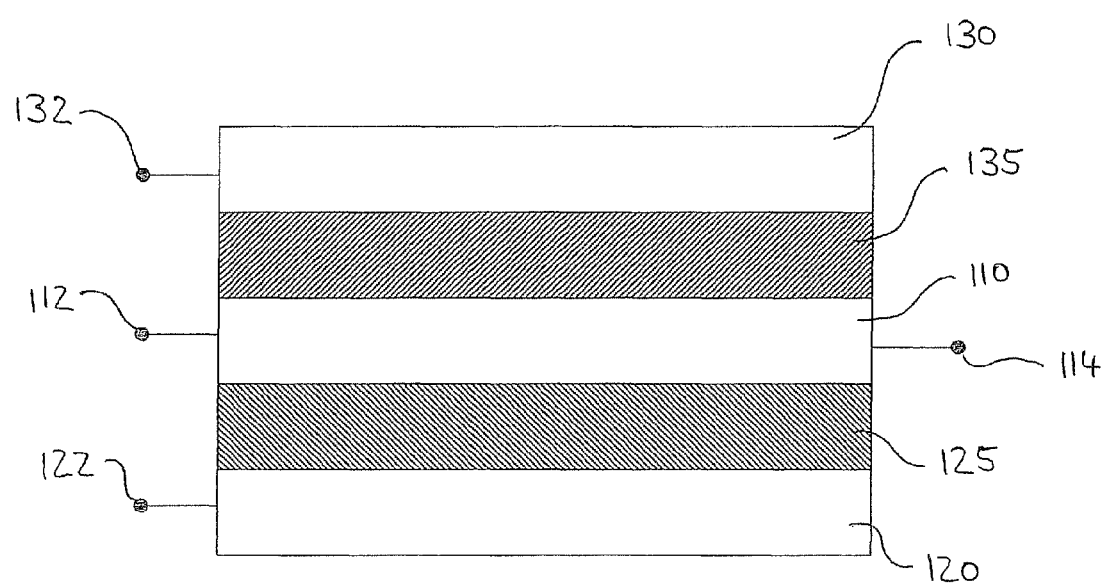
FIG. 1 illustrates a sensor of the medical treatment device according to embodiments of the present invention.

Embodiments include, as the impedance means, a capacitive sensor or an inductive sensor (induction element) or a combination thereof, for example.

In embodiments in which the impedance means are configured as a capacitive sensor, the first, the second and the third dielectric material may in particular have different relative dielectric constants. Optionally, it is also possible that the first and the second dielectric material form a common layer and therefore have the same dielectric constant so that the first contact electrode is formed on the layer on one side and the second and the third contact electrode are formed on the opposite side in such a way that they are laterally offset from each other. In further embodiments, additional dielectric layers may be formed below the third dielectric material or between the first and the second contact electrode, for example, which also have different dielectric constants in order to suppress interference capacitances, for example. Optionally, it is also possible to configure the capacitive sensor of the medical treatment device by means of a printed circuit board on which the first to fourth contact electrode and the first to third dielectric material are stacked as layers on top of one another or that the printed circuit board itself represents one of the dielectric layers (i. e. the first to third dielectric material). Also possible is a coaxial arrangement in which the individual contact electrodes are arranged to each other in the form of a (semi)cylinder at different distances in the radial direction and are isolated from each other by dielectric layers so that the dielectric layers may also be arranged coaxially to each other. The advantages of these embodiments are that simple means (such as printed circuit boards) may be utilized and that positioning (e. g. in the case of a coaxial arrangement within a power supply line) can be done in a flexible manner.

In embodiments in which the impedance means are configured as an induction element, the cross-sectional area of the induction element may be selected smaller than the cross-sectional area of the first planar electrode by at least a factor of 10 (or by one of the following factors: 2, 5, 20, 50, or 100) and the surface area of the first planar electrode and that of the induction element which face each other should be selected small. This is to achieve that the capacitive coupling between the first or the second planar electrode towards the induction element is minimized but, at the same time, that the inductive coupling between the first planar electrode and the induction element can be maximized, as the inductive coupling depends only on the number of turns and the enclosed area (again in the case that the cross-sectional area which may be selected according to the current density is constant).

In further embodiments, the first planar electrode is arranged between the second planar electrode and the induction element. Optionally, the first planar electrode and the second planar electrode may be wound around a soft magnetic coil core or may be embedded at least partially in a soft magnetic material. This is to improve the magnetic coupling between the two planar coils (i. e. between the first planar electrode and the induction element) and, at the same time, screening with regard to external electromagnetic fields is effected.

In further embodiments, the second planar electrode and the induction element are arranged laterally adjacent to each other and are isolated from the first planar electrode by a common dielectric layer (common layer of dielectric material) so that the first planar electrode is formed on one side of the common dielectric layer and the second planar electrode and the induction element are arranged on the opposite side (but laterally offset from each other). This allows to further decrease the component size and, in particular, the height of the component is further minimized so that the component may be mounted in different positions of the medical treatment device in a flexible manner (e. g. the component may be integrated into the hand-piece or power supply line).

In further embodiments, the first planar electrode has a first portion and a second portion. The first portion may optionally be designed as a capacitor plate and the second portion may be wound to form a planar coil, the two portions being electrically interconnected by a junction. In these embodiments, the second planar electrode and the first portion, for example, may be arranged on opposite sides of the first dielectric material in such a way that the capacitive coupling between them is maximized. In the same way, the induction element and the second portion are arranged on opposite sides of the second dielectric material in such a way that their inductive coupling is maximized if possible. In this embodiment, it is possible to physically separate the capacitive coupling from the inductive coupling so that their interaction/interference can be minimized. Optionally, this effect may be further improved by an additional screening between the two sensor portions. Moreover, this allows the component height to be reduced, as the two sensor portions can be arranged adjacent to each other. Optionally, the induction element may be wound into a coil having a clearly increased winding number so that the additional height required in this case is not at the sacrifice of the total component height.

Here and in the following, the term "lateral" refers to the areal configuration in which two elements are arranged laterally adjacent to each other, if the two elements appear perpendicular to a signal propagation direction (input signal or capacitive/inductive measuring signal) vertically at the same level in a cross-sectional view. The vertical direction may be defined by the face normal of one of the main surfaces of the areal configuration. The term "planar" (in "planar electrode", "planar coil") refers in the same way to an areal configuration. "Areal" configuration means any configuration in which the orientation of the face normal in at least one main direction of extension (which is at least 5% of the maximum extension of the relevant object) does not change by more than 10° (or more than 20° or 50°). Alternatively, a planar electrode may be defined as being suitable as a capacitor plate and as providing a capacitive signal which can be detected by the medical treatment device. Therefore, coaxial arrangements are also covered. Planar coils may be defined, for example, as coils which are wound mainly in one plane. The plane, in turn, may be defined as a plane which has a face normal whose orientation does not change by more than 10° (or changes by not more than 20° or not more than 50°) during a movement in at least one direction. The orientation, in turn, defines the direction in the three-dimensional space. The term "elongated" defines a geometrical configuration in which the element has a maximum extension which exceeds the minimum extension by at least two times or ten times or 100 times, the maximum and minimum extensions being measured in different directions in space.

In further embodiments, the related dielectric materials have different relative dielectric constants and/or different relative magnetic permeabilities. The medical treatment device according to the invention and the integrated sensor allow, for example, voltage and current to be measured independently on each other, a capacitive measurement and an inductive measurement being used for the two measurements.

In further embodiments, the current path input and the current path output may have a minimum distance from each other, which may be larger than 1 mm, 2 mm or larger than 10 mm or larger than 20 mm or larger than 30 mm. This physical separation has the advantage that high-frequency harmonic waves, for example, can be detected whose occurrence is an indication of an undesired non-resonant operation.

Concrete realizations will be described by means of the following figures.

FIG. 1 illustrates a sensor for a medical treatment device according to an embodiment of the present invention, a first electrode 110 having a current path input 112 and a current path output 114. The electric input signal for powering the medical treatment device 100 is applicable to the current path input 112 and a load of the medical treatment device 100 can be coupled to the current path output 114. In addition, the sensor includes a second electrode 120 which is electrically isolated from the first electrode 110 by a first dielectric material 125, the second electrode 120 having a measuring signal terminal 122. Further, the sensor includes impedance means 130 which are electrically isolated from the first electrode 110 by a second dielectric material 135. The impedance means 130 include at least one measuring signal terminal 132 to obtain a second sensor signal. In this sensor, the first electrode 110 is configured to have a cross section which is formed perpendicular to the direction of propagation of the electric input signal in such a way that the first electrode 110 and the second electrode 120 couple to provide a capacitive measuring signal (or, generally, an impedance) as a first measuring signal (sensor signal). The impedance means 130 are configured in the form of a structural electrode so that the first electrode 110 and the impedance means 130 couple to provide an impedance (or, generally, an additional impedance) as a second measuring signal (sensor signal).

FIGS. 2 through 13 illustrate embodiments in which the impedance means are given by an induction element.

Figure 2:
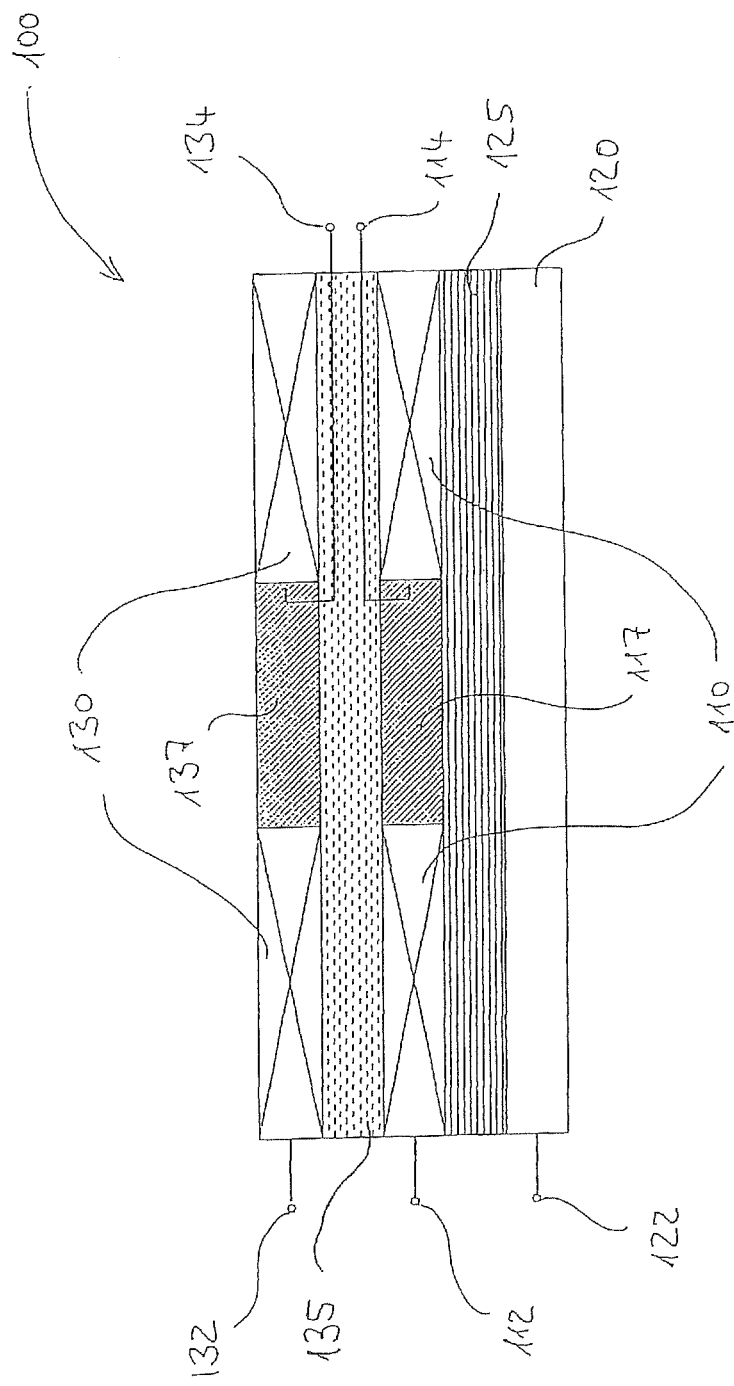
FIG. 2 illustrates a sensor of the medical treatment device according to a further embodiment of the present invention.

FIG. 2 illustrates an embodiment of a medical, in particular dental, treatment device 100 having a sensor for the detection of operating states, which includes a first planar electrode 110 arranged between the current path input 112 and the current path output 114, an electric input signal for powering the medical treatment device being applicable to the current path input 112 and a load of the medical treatment device 100 being applicable to the current path output 114. The first planar electrode 110 is configured as a first planar coil (by winding or printing, for example). The device 100 further includes a second planar electrode 120 which is isolated from the first planar electrode 110 by a first dielectric material 125 and includes a first measuring signal output 122 for picking off a capacitive measuring signal. The device 100 further includes an induction element 130 (as the impedance means) which is isolated from the first planar electrode 110 by a second dielectric material 135 and is formed between a second measuring signal terminal 132 and a third measuring signal terminal 134. An inductive measuring signal can be picked off between the second measuring signal terminal 132 and the third measuring signal terminal 134. In the device 100, the first planar electrode 110 has an elongated cross section in the planar direction of the first planar coil so that the first planar electrode 110 and the second planar electrode 120 can be coupled capacitively and the first planar electrode 110 and the induction element 130 can be coupled inductively.

Optionally, the first planar electrode 110 which is configured as a planar coil may include a first coil core 117 (e. g. of a soft magnetic material or of another dielectric material). Similarly, the induction element 130 may be configured as a second planar coil (i. e. it may be wound planarly) and may include a second coil core 137 which may include a soft magnetic material or a dielectric material as well. The first and the second coil core 117, 137 allow an improved inductive coupling between the first planar electrode 110 and the induction element 130. Optionally, it is also possible to form the second dielectric material 135 not over the entire area but to form it only between the windings of the coils (which are represented by the crossed areas). A soft magnetic material or another magnetic material may be also formed between the first coil core 117 of the first planar electrode 110 and the second coil core 137 of the induction element 130 to improve the inductive coupling between the planar coils of the first planar electrode 110 and the induction element 130. Other magnetic materials (e. g. various forms of ferrites) may be also used to improve the magnetic coupling.

Figure 4:
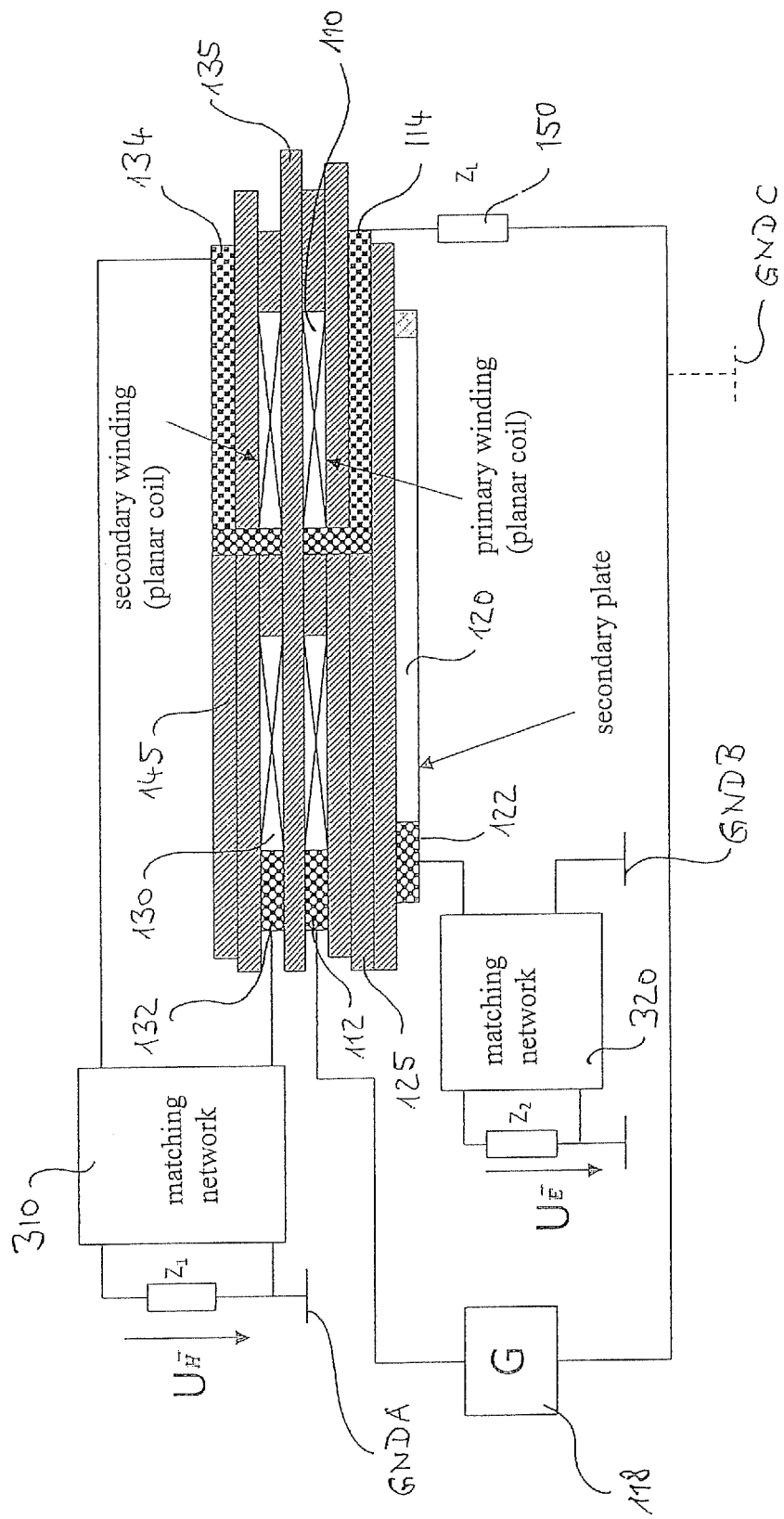
FIG. 4 illustrates a side view of a multilayer printed circuit board (multilayer PCB) according to an embodiment.

The current path output 114 and the third measuring signal terminal 134 couple, for example, to a (radial) inner surface of the first and the second planar coil and connecting lines may be laid, for example, through one of the dielectric layers (e. g. through the second dielectric material 135). An alternative approach is shown in FIG. 4.

The first and the second planar coil, which are shown in the cross-sectional view of the Figures, form electrically conductive turns/windings which are not illustrated individually for the sake of simplicity and only the cross-sectional space occupied by the windings (crossed areas) is shown.

Figure 3:
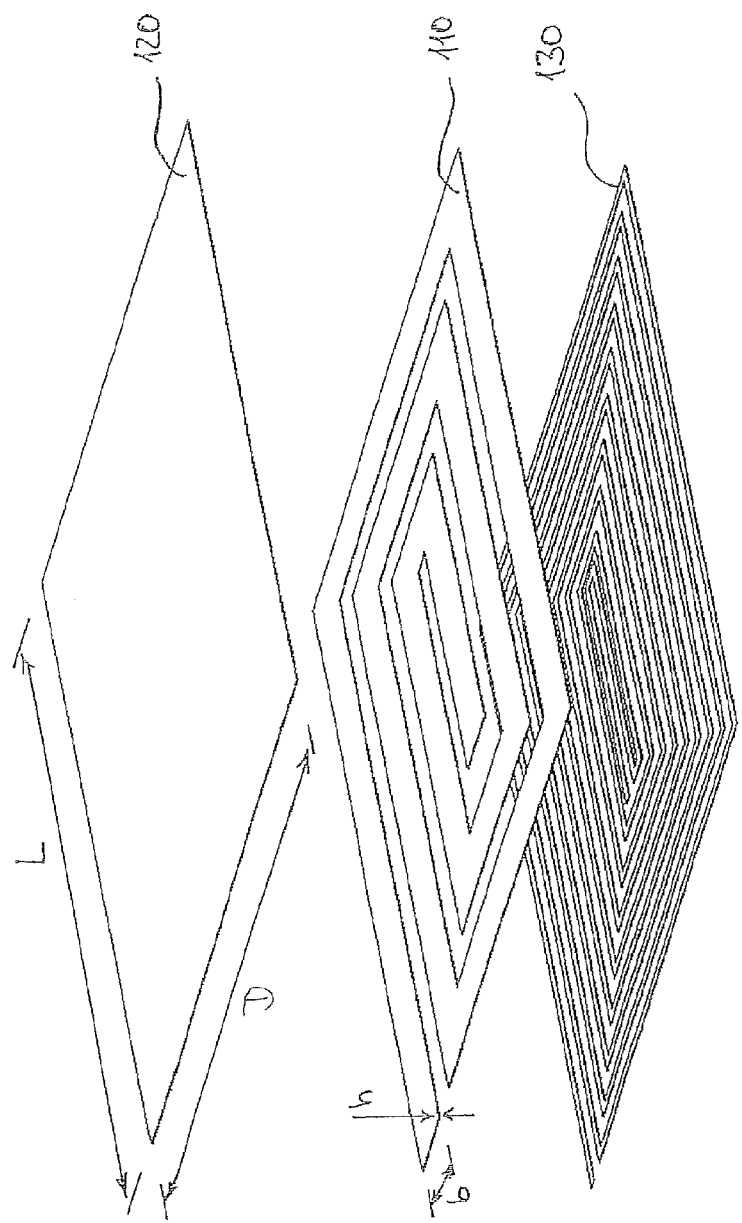
FIG. 3 illustrates the fundamental principle of the sensor according to embodiments.

FIG. 3 illustrates a perspective view of each of the planar electrodes, the first planar electrode 110 being arranged between the second planar electrode 120 and the induction element 130. In the perspective view shown in FIG. 3, the induction element 130 is arranged at the bottom, whereas the second planar electrode 120 is arranged at the top (in contrast to the embodiment shown in FIG. 2). In this case, the second planar electrode 120 forms a secondary plate, for example, which detects a capacitive field component and is configured as a capacitor plate, for example. The first planar electrode 110 is configured as a planar coil and forms the primary winding (primary plate), as the measuring signal to be measured primarily is passed through the first planar electrode 110, the current path input being arranged at the outermost coil end, for example, and the current path output being arranged at the inner coil end. In further embodiments, the current path input may be, of course, replaced with the current path output so that the measuring signal to be measured is coupled to the inner surface of the coils and is appropriately picked off at the outer coil side. As appears from FIG. 3, the first planar electrode 110 is formed flat so that a highest possible capacitive coupling between the second planar electrode 120 and the first planar electrode 110 can be produced. This may be achieved, for example, by making the cross section of the first planar electrode 110 rectangular (or oval), the longer side of the rectangle being aligned in parallel to the planar extension of the second planar electrode 120 (secondary plate).

The induction element 130 is arranged below the first planar electrode 110 in FIG. 3 and is also configured as a planar coil (secondary winding). By means of the induction element (secondary winding), an inductive field component can therefore be picked off, which results from an inductive measuring signal generated in the induction element 130 due to the induction when a signal to be measured is passed through the first planar electrode 110. The induced measuring signal can be influenced by appropriately selecting the winding number of the induction element 130 (secondary winding). In order to suppress, if possible, a capacitive coupling between the first planar electrode 110 and the induction element 130, for example (or between the second planar electrode 120 and the induction element 130), the induction element 130 is optionally configured to have a cross section which, in contrast to the first planar electrode 110, has a reduced common area with the first planar electrode 110. The induction element 130 may be configured in the form of wires (e. g. with a square or round cross section), for example, so that there is mainly only an inductive coupling between the first planar electrode 110 and the induction element 130 and a capacitive coupling, which might exist, is suppressed to a large extent if possible.

The fundamental principle described above may be effected through the following possible geometries, for example. First, the winding number and the overall geometry may differ, depending on the range of frequencies. In the primary winding (planar coil) of the inductive sensor portion as is provided by the first planar electrode 110, the winding number may be 8, for example (other possible values are 6, 7, 9, 10, 20, or less than 10), and the cross section of the conductor path may have a height h of 35 μm and a width b of 0.5 mm, for example, the cross sections relating to each winding. However, these values can be varied according to the current density, as the main current of the exemplary piezoelectric motor, which must also pass the primary windings, flows through the first planar electrode 110. The cross-sectional area b×h (perpendicular to the direction of current) is fixed based on the current density, for example, and may remain fixed, for example, whereas the width b and the height h are varied in relation to each other to optimize the capacitive and inductive couplings. For example, the capacitive coupling between the primary winding and the secondary plate (second planar electrode 120) may be improved by increasing the conductor path width b. The overall geometry of the first planar electrode 110 may have a length L of 25 mm and a width D of 15 mm, for example.

The induction element 130 forms the secondary winding, which is also configured as a planar coil and is part of the inductive sensor portion. The winding number of the induction element 130 is, for example, 15 (other values are, for example, 10, 11, 12, 20, 25, or 30, or more than 10, or less than 10), the cross section of the conductor path of the induction element 130 having, for example, a height h of 35 μm and a width b of 0.1 mm (height h and width b are, for example, measured in the same way as in the first planar electrode 110), these values relating to each winding. As the current density in the induction element 130 is, for example, less than in the primary winding 110, the conductor path of the secondary winding may, for example, have smaller dimensions, e. g. a smaller layer thickness h or a smaller width b. The overall geometry may, for example, correspond to the overall geometry of the primary winding (first planar electrode 110) so that here again a total length L of 25 mm and a total width D of 15 mm are possible (i. e. the induction element 130 wound to form a planar coil has an area of 25 mm×15 mm) but it may also be selected larger than or less than the first planar electrode 110.

The second planar electrode 120 forms the secondary plate and forms together with the first planar electrode 110, which acts as a primary plate, the capacitive sensor portion (i. e. the first planar electrode 110 is both part of the capacitive and of the inductive sensor portion). The layer thickness h is 35 μm, for example. As the current density of the secondary plate is also smaller than the current density of the first planar electrode 110, the area or thickness of the conductor path may be also selected smaller (i. e. it may have a layer thickness smaller than 35 μm). For example, the overall geometry may be selected equal to the overall geometry of the primary winding/plate or of the secondary winding of the inductive sensor portion so that the capacitive sensor portion may also have a layer thickness L of 25 mm, for example, and a width B of 15 mm.

The length L may be less than 25 mm or larger than 25 mm, for example, and the total width D may similarly be less than 15 mm or larger than 15 mm. Similarly, the height h may be less or larger than 35 μm and the width b may also be larger or less than 0.5 mm or larger or less than 1 mm. As the material for the secondary plate, copper may be used, for example.

FIG. 4 illustrates a side view of a multilayer PCB in which the first planar electrode 110 is arranged between the second planar electrode 120 and the induction element 130, a first dielectric material 125 being formed between the first planar electrode 110 and the second planar electrode 120. In the embodiment shown in FIG. 4, the first dielectric material 125 is formed by a plurality of dielectric layers, one of the layers including a current path output 114 formed as a conductive layer, which contacts an inner portion of the coil of the first planar electrode 110. A second dielectric material 135 is formed between the first planar electrode 110 and the induction element 130. In the embodiment shown in FIG. 4, another dielectric material 145, which may optionally also include a plurality of layers, is formed above the induction element 130. The induction element 130 is configured as a second planar coil and is contacted by the second measuring signal terminal 132 at an outer surface of the coil and is contacted by the third measuring signal terminal 134 at the inner surface of the coil. The third measuring signal terminal 134 is formed as a conductive layer (as is the current path output 114), which first extends in parallel to the induction element 130 and then is led into the inner portion of the coil.

Each dielectric layer and the planar electrodes may be formed as (printed) conductor paths, for example, an electrically conductive material such as copper being used for the planar electrodes and an electrically insulating material such as printed circuit boards (material used for printed circuit boards), plastics or ceramics being used for the dielectric materials. The current path input 112 is connected to a generator 118 (e. g. a vibration generator or a power supply unit), which, in turn, is electrically connected to a load 150 (e. g. a piezoelectric motor), which is connected in series between the current path output 114 and the generator 118. The load has an impedance $Z_L$, for example. Between the second measuring signal terminal 132 and the third measuring signal terminal 134, a first matching network 310 is connected, which measures a voltage $U_H$ as an inductive measuring signal by measuring a voltage drop across a first impedance $Z_1$ (for example, in relation to a first reference potential GNDA to be applied to one side of the impedance), the inductive measuring signal depending on the parameter (current/voltage) induced in the induction element 130. The first measuring signal output 122 is coupled to a second matching network 320 which includes a second impedance $Z_2$ and a second reference potential GNDB. The second matching network 320 provides a voltage signal $U_E$ (e. g. in relation to the second reference potential GNDB) as a capacitive measuring signal. The first matching network 310 and the second matching network 320 may have amplifiers and/or filters and/or A-D converters, for example, which are used to process or to amplify or to filter the measured signals appropriately to subsequently convert them into a control signal, by means of which the electric supply signal is influenced.

The electric connection between the generator 118 and the load 150 may be at a third reference potential GNDC, for example, which corresponds to the first or second reference potential GNDA, GNDB but may optionally be selected different. In this case, selecting the reference potentials (GNDA, GNDB, GNDC) different may serve as a galvanic isolation of the individual components or of the evaluation circuit.

Figure 5:
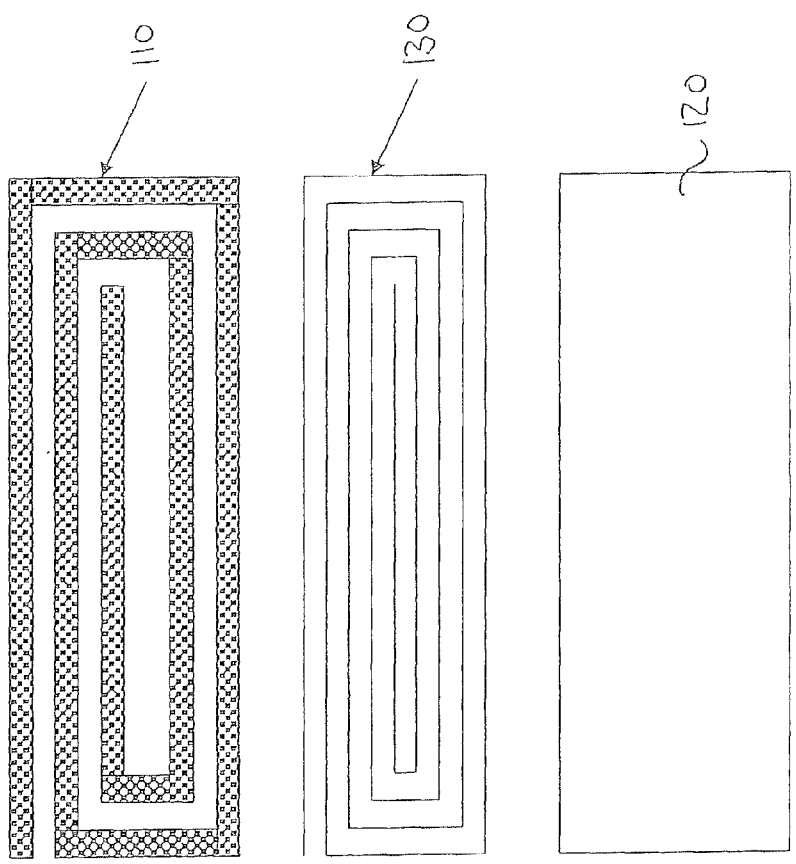
FIG. 5 illustrates top views of the primary and secondary windings and of the secondary plate.

FIG. 5 illustrates a top view of the primary and secondary windings (of the planar coils) and of the secondary plate. First, the primary winding, which is given by the first planar electrode 110, is shown at the top. This planar electrode is configured flat and forms an electrically conductive region and may be defined, for example, by a printed conductor. The flat configuration of the first planar electrode 110 serves the capacitive coupling to the secondary plate (second planar electrode 120) and serves, at the same time, the inductive coupling (inductive field component) to the induction element 130 through the windings formed.

In the center of FIG. 5, a secondary winding is shown, which provides an inductive coupling for the primary winding so that a magnetic field component can be detected. The secondary winding (induction element 130) is, for example, configured by thin electric regions which may also include printed copper conductors, for example. In comparison to the primary winding, the area of the secondary winding shown in the top view is clearly smaller than in the primary winding, i.e. the corresponding copper conductors are formed thinner, or the primary winding includes a plurality of copper conductors running in parallel to increase the area in the planar directions. The thin, electrically conductive regions of the secondary winding (induction element 130) are, for example, selected in such a way that almost no capacitive field component is obtained. This is to detect only the magnetic field component in relation to the flat primary winding (first planar electrode 110) if possible. The configuration of the coil of the primary and secondary windings, as they are shown in FIG. 5, may optionally be circular, elliptical, rectangular or square or may have another form and the configuration must only ensure that the inductive coupling between the primary winding and the secondary winding is optimal if possible.

At the bottom of FIG. 5, the secondary plate is shown, which serves the capacitive coupling between the first planar electrode 110 and the second planar electrode 120 to obtain the electrical field component. The secondary plate, as it is shown at the bottom of FIG. 5, may be, for example, an electrically conductive surface and may be defined by printed copper conductors, for example. As the primary winding is configured flat, almost only the capacitive field component in relation to the secondary plate is detected.

It is an advantage of this overall configuration that electric and magnetic fields can be detected simultaneously. This allows any phase shift to be detected, depending on the load impedance. Optionally, an amplitude for current and/or a voltage amplitude and/or a frequency may also be detected at the same time.

FIGS. 6A and 6B illustrate side views of other embodiments in which the induction element 130 is not configured as a planar coil but as a usual coil which is also wound in the direction perpendicular to the planar plane (windings are not only located in a common plane). The planar plane is given by the length L and the width D shown in FIG. 3.

FIG. 6A shows an embodiment in which the induction element 130 is wound as a coil around a soft magnetic coil core 137 in such a way that the lateral extension of the induction element 130 is smaller than the lateral extension of the first planar electrode 110 which is isolated from the induction element 130 by the second dielectric material 135. The secondary plate 120 (second planar electrode) serves again the provision of the capacitive field component to the first planar electrode 110 and has, in the embodiment shown in FIG. 6A, a smaller surface area than the one occupied the first planar electrode 110, the surface areas relating to the planar extension. The first planar electrode 110 serves again as a primary winding (as it is configured as a planar coil) to produce the inductive field component for the induction element 130. The dielectric materials used between the induction element 130 and the first planar electrode 110 as well as between the second planar electrode 120 and the first planar electrode 110 may include the same or different electrically insulating materials, whereas the coil core 137 of the induction element 130 may include, for example, a soft magnetic core material such as ferrites.

The difference between the embodiment shown in FIG. 6B and the embodiment shown in FIG. 6A is that the secondary plate 120 and the induction element 130 are arranged laterally adjacent to each other, namely on the same side of the dielectric layer 135 as the induction element 130. On the common dielectric layer 135, only the first planar electrode 110 (primary winding, planar coil) is therefore arranged on one side and both the second planar electrode 120 and the induction element 130 (e.g. wound to form a coil) are arranged on the opposite side. In the embodiment shown in FIG. 6B, a soft magnetic material 137 is formed again in the coil core of the induction element 130. The secondary plate (second planar electrode 120) may be arranged, for example, as a ring surface around the induction element 130 to ensure, on the one hand, the largest possible capacitive coupling between the second planar electrode 120 and the first planar electrode 110 and, on the other, the largest possible inductive coupling of the first planar electrode 110 to the induction element 130 and/or to allow a reduction in the size of the geometry of the coil and/or matching to the ranges of frequency.

Optionally, a first coil core 117 is included in the center of the first planar electrode 110 may also include a soft magnetic or dielectric material.

Figure 7:
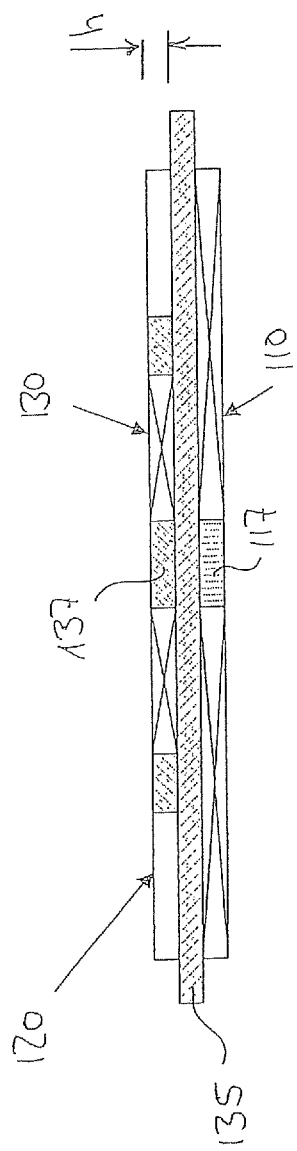
FIG. 7 illustrates a side view of an embodiment in which the second planar electrode and the induction element are arranged side by side.

FIG. 7 illustrates a further embodiment in which the second planar electrode 120 and the induction element 130 are arranged laterally adjacent to each other on a common side of the dielectric layer 135. In the embodiment shown in FIG. 7, the induction element 130 has only the same height h as the second planar electrode 120. In addition, in the embodiment shown in FIG. 7, the coil core 137 in the induction element 130 is not composed of a soft magnetic material (but e.g. of an insulating material). The first planar electrode 110 is arranged again on the opposite side of the dielectric layer 135, the lateral extension of the first planar electrode 110 coinciding with the common lateral extension of the second planar electrode 120 and of the induction element 130, for example. The embodiment shown in FIG. 7 has, therefore, a very small total height and can hence be easily integrated in different positions of the treatment device.

Figure 8:
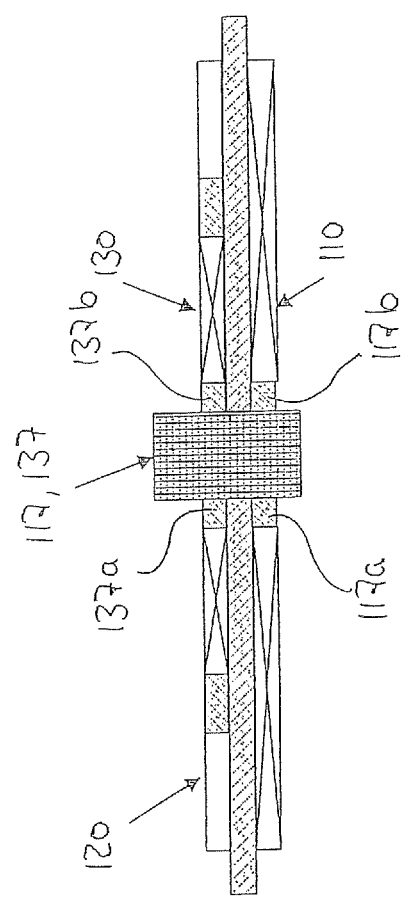
FIG. 8 illustrates a side view of the embodiment illustrated in FIG. 7 using a soft magnetic coil core.

The difference between the embodiment shown in FIG. 8 and the embodiment shown in FIG. 7 is that a common magnetic coil core 137, 117 is formed in the first planar electrode 110 and the induction element 130 so that the primary winding and the secondary winding have a common coil core which serves an improved magnetic coupling between the two planar coils. Similarly to the embodiment shown in FIG. 7, the second planar electrode 120 is arranged outside of the induction element 130 as seen from the common coil core 117, 137 (it is arranged in the form of an annulus, oval, rectangle or square around the induction element, for example). It is optionally possible to form another dielectric material 137a, b and 117a, b between the coil core 137, 117 and the windings of the first planar electrode 110 and of the induction element 130. The soft magnetic coil core 117, 137 may be screwed into the substrate (printed circuit board). This is to improve the coupling between the primary and the secondary winding. Another advantage of this embodiment (as well as of that shown in FIG. 7) is simplified contacting, as the inner surfaces of the coil are accessible and the current path output 114 and the third measuring signal terminal 134 can be formed easily without interfering with other components.

FIG. 9 illustrates a further embodiment in which the induction element 130 is embedded in an encasement 139 (made of a soft magnetic material, for example). As before, a first dielectric material 125 is formed between the first planar electrode 110, which forms again the primary winding for the inductive field component, and the second planar electrode 120 (for the capacitive field component) and a second dielectric material 135 is formed between the first planar electrode 110 and the induction element 130. The dielectric layers may again be printed circuit boards, for example. The encasement 139 may include, for example, all sides of the induction element 130 except the direction towards the first planar electrode 110. Optionally, a mounting bracket 138 may retain the encasement 139. For example, in the dielectric layers (which are given by printed circuit boards, for example), an opening may be formed, through which the mounting bracket 138 extends so that the encasement 139 can be firmly connected to the sandwich structure lying underneath (dielectric layers and the first and the second planar electrode). In the embodiment shown in FIG. 9, the induction element 130 is formed with a square cross-sectional area which is surrounded by the encasement 139.

It is an advantage of using a soft magnetic material for the encasement 139 that the inductive coupling between the primary and the secondary winding is thereby improved. In addition, a firm hold to the printed circuit board (substrate) can be achieved by means of the mounting bracket 138. It is further advantageous that an improved EMC protection (EMC: electromagnetic compatibility) is achieved in the embodiment shown here.

FIGS. 10A, B illustrate further embodiments in which the encasement 139 in a multilayer PCB is produced by using a ferrite material. The ferrite material is also used for the coil core 139a of the induction element 130 formed as a coil and it is formed as a ferrite layer 139b along the top surface.

In FIG. 10A, additional soft magnetic elements 139c, d are formed at the outer periphery (i. e. they are formed laterally adjacent to the induction element 130). As a result, the induction element 130 is surrounded by the layers 139c, d, which are made of a soft magnetic material, both at the top (by the layer 139b) and at the side. The remaining components of the embodiment shown in FIG. 10A do not differ from those of the embodiment shown in FIG. 9 so that the description is not repeated here. In the embodiment shown in FIG. 10B, the side elements 139c and 139d are not made of a ferrite material but from a dielectric material, for example. All the other components of the embodiment shown in FIG. 10B are in agreement with the components described above.

An advantage of the at least partial embedment of the secondary winding 130 in a soft magnetic material (such as ferrite) is an increased EMC protection. In addition, a further integration of the components and hence an increased robustness are achieved. Optionally, the ferrite segments may be made of different types of ferrite to obtain the desired frequency response or to avoid undesired EMC effects.

Figure 11:
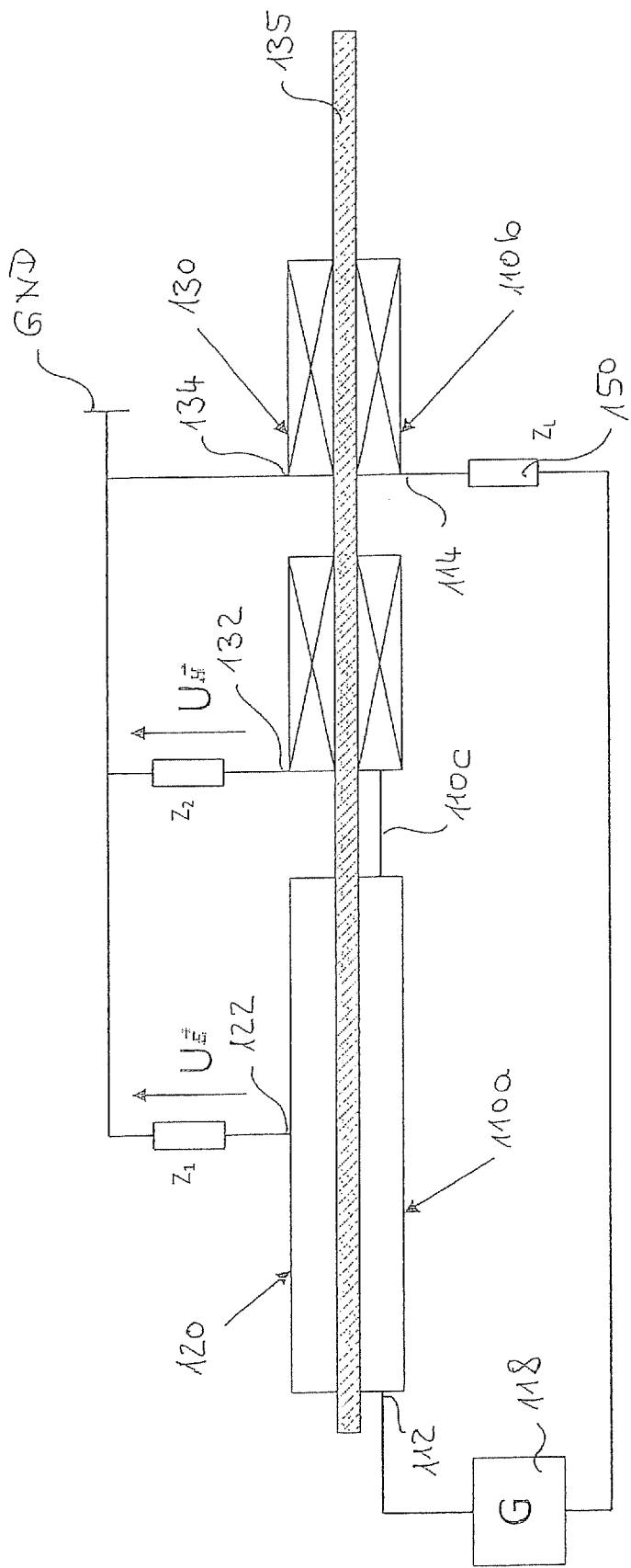
FIG. 11 illustrates a side view of an embodiment in which the planar electrodes are arranged in a laterally offset manner along a common dielectric material.

FIG. 11 illustrates an embodiment in which all elements are formed again along a common dielectric layer 135. In addition, the first planar electrode 110 includes a first portion 110a and a second portion 110b. On one side of the common dielectric layer 135, the second planar electrode 120 and the induction element 130 are arranged laterally separated from each other. The first portion 110a is configured as a primary plate and is arranged opposite the second planar electrode 120 on the other side of the common dielectric layer 135. The second portion 110b is electrically contacted to the first portion 110a and is arranged laterally offset from the first portion 110a on the same side of the common dielectric layer 135, namely opposite the induction element 130, so that an inductive field component may be read out by the induction element 130.

A first impedance $Z_1$ may be connected between the first measuring signal terminal 122 at the second planar electrode 120 and a reference potential GND and the capacitive measurand $U_E$ may be determined, for example, as a potential drop through the first impedance. The inductive field component may be determined, for example, by means of a second impedance $Z_2$ (e. g. again as a potential drop $U_H$), which is formed in series between the second and the third measuring signal terminal 132, 134 (optionally, the second or the third measuring signal terminal 132, 134 is also at the reference potential GND). The current path input 112 is arranged on the first portion 110a and the current path output 114 is arranged on the second portion 110b, a generator 118 and a load impedance $Z_L$ (load 150) being connected in series between the current path input 112 and the current path output 114. The load 150 may include a piezoelectric element of the treatment device.

Figure 12:
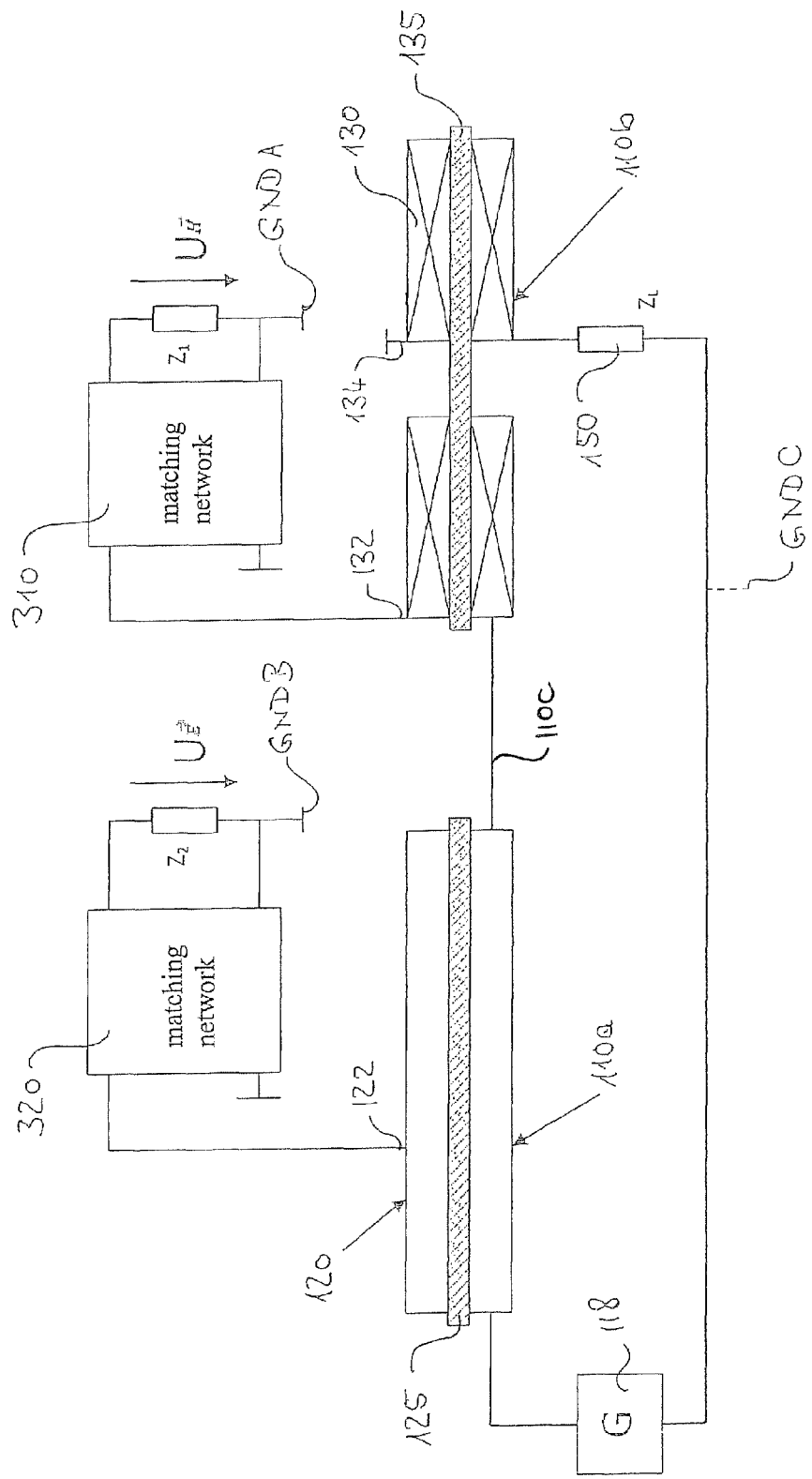
FIG. 12 illustrates a side view of an embodiment in which the respective sensor components are spaced apart from each other.

In the embodiment shown in FIG. 12, no common dielectric layer is formed, the first planar electrode 110 including again a first portion 110a and a second portion 110b which are connected to each other through an electrical connection 110c.

The capacitive sensor portion is therefore given by the first portion 110a of the first planar electrode 110 and the second planar electrode 120 which are arranged on opposite sides of the first dielectric layer 125. The inductive sensor portion is given by the second portion 110b and the induction element 130 which are arranged opposite each other on different sides of the second dielectric layer 135.

The electrical connection 110c between the second portion 110b and the first portion 110a of the first planar electrode 110 may be formed, for example, in such a way that the capacitive sensor portion is arranged in a component which is different from that of the inductive sensor portion. Accordingly, the acquisition of measured values may also be carried out separately from each other. At the second measuring signal terminal 132 of the induction element 130, the first matching network 310 may be arranged (see also FIG. 4) which is connected in relation to a first reference potential GNDA and measures a voltage drop $U_H$, for example, through a first impedance $Z_1$ according to a magnetic field component. The second measuring signal terminal 134 is also at a reference potential which optionally coincides with the first reference potential GNDA. For the capacitive measurement, the second matching network 320 is coupled to the first measuring signal output 122, which measures a voltage drop, for example, through a second impedance $Z_2$ and determines, from the result of measurement, the electric field strength, for example. As is shown in FIG. 12, a generator 118 and a load impedance $Z_L$ are connected between the current path input 112 and the current path output 114, the node between them being at the third reference potential GNDC so that isolation is effected. Optionally, the reference potentials may be selected either equal or different.

In this embodiment, the capacitive sensor portion and the inductive sensor portion are spaced apart from each other. For example, one of the two sensor portions may be arranged in the hand-piece of the treatment device or in the connecting line, whereas the other of the two sensor portions is accordingly accommodated in the connecting line or in the power supply unit. Embodiments include therefore the following options. The capacitive sensor portion is arranged in the hand-piece, whereas the inductive sensor portion is arranged in the connecting line or in the power supply unit. In another embodiment, the capacitive sensor portion is arranged in the connecting line, whereas the inductive sensor portion is arranged in the hand-piece or in the power supply unit. In another embodiment, the capacitive sensor portion is arranged in the power supply unit, whereas the inductive sensor portion is arranged in the hand-piece or in the connecting line. In addition, in further embodiments, the capacitive and the inductive sensor portion may be arranged together in the hand-piece or together in the power supply unit or together in the connecting line.

Figure 13:
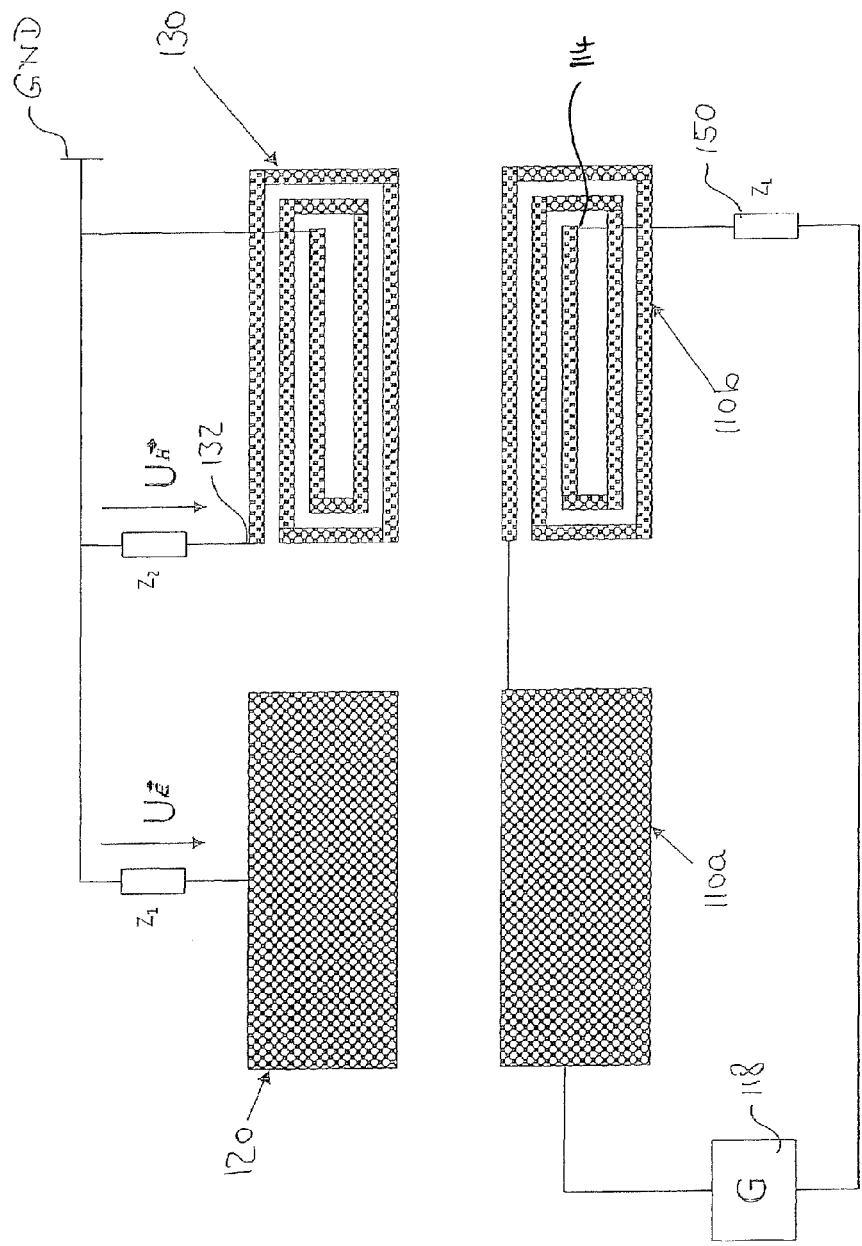
FIG. 13 illustrates top views of the primary side and of the secondary side of the embodiment of FIG. 11 or 12.

FIG. 13 illustrates top views of the secondary side (as a top layer) and of the primary side (as a bottom layer). On the secondary side (at the top), the secondary plate 120 and, adjacent to it, the secondary winding (the induction element 130) are shown. On the primary side (at the bottom), the primary plate 110a given by the first portion 110a of the first planar electrode 110 is shown and, adjacent to it, the second portion 110b of the first planar electrode 110 is shown as a primary winding. The capacitive sensor is given by the secondary plate 120 and the primary plate 110a and the inductive sensor is given by the primary winding 110b and the secondary winding 130. In the embodiment shown in FIG. 13, the load is connected between the current path output 114 of the primary winding 110 and the generator 118, the generator 118 being, in turn, electrically coupled to the primary plate 110a. The two measuring signals are measured in relation to a common reference potential GND (as in FIG. 11), the electrical component being measured through an impedance $Z_1$ between the secondary plate 120 and the reference potential GND and the magnetic field component being measured by means of a voltage drop through a second impedance $Z_2$ connected between the second measuring signal terminal 132 and the reference potential GND.

In further embodiments, the impedance means are configured as one or more additional capacitive sensors.

Figure 14:
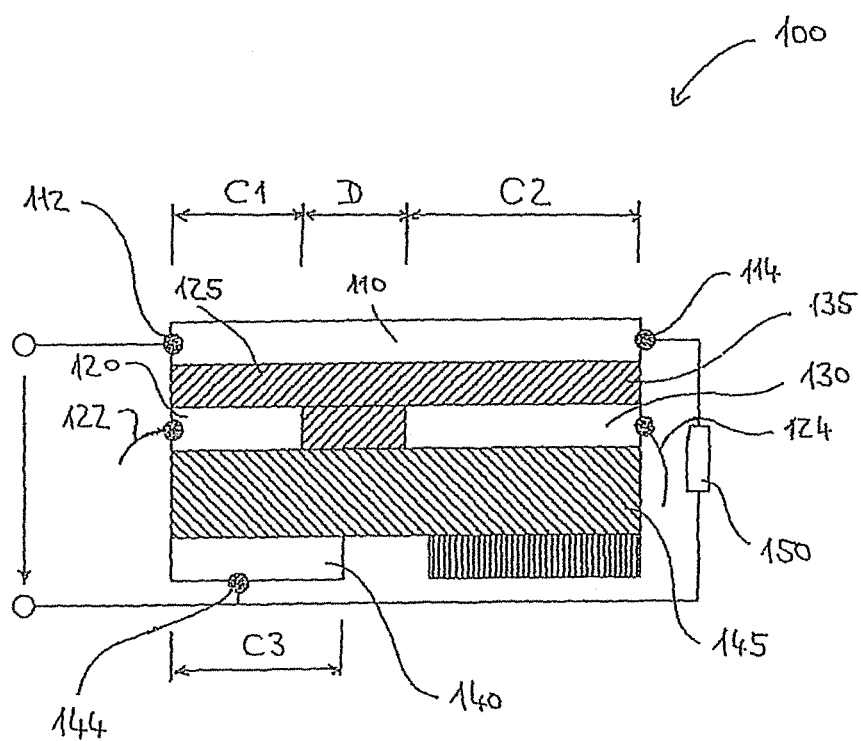
FIG. 14 illustrates a sensor of a medical treatment device according to a further embodiment of the present invention.

FIG. 14 illustrates an embodiment for such a purely capacitive sensor for a medical treatment device 100. The capacitive sensor includes a first contact electrode 110 extending between the current path input 112 and the current path output 114, an electric input signal for powering the medical treatment device being applicable to the current path input 112 and the load 150 of the medical treatment device being applicable to the current path output 114. The treatment device 100 further includes a second contact electrode 120, which is isolated from the first contact electrode 110 by a first dielectric material 125, and a first measuring signal output 122 for picking off a first capacitive measuring signal. Further, a third contact electrode 130 is formed, which is isolated from the first contact electrode 110 by a second dielectric material 135 and includes a second measuring signal output 124 for picking off a second capacitive measuring signal. A fourth contact electrode 140 is isolated from the second contact electrode 120 by a third dielectric material 145 and includes a reference terminal 144 for coupling to a ground potential.

In the embodiment shown in FIG. 14, the first and the third dielectric material 125, 135 form a common dielectric layer, which will be also referred to as a first dielectric layer 135 below.

The region in which the first contact electrode 110 and the second contact electrode 120 are arranged opposite the first dielectric layer 135, forms a first capacitor region C1 and, laterally offset from it, a second capacitor region C2 is defined by the region in which the third contact electrode 130 and the first contact electrode 110 are arranged on opposite sides of the first dielectric layer 135. Finally, a third capacitor region C3 is formed by the lateral extension of the fourth contact electrode 140 which is arranged opposite the second contact electrode 120 with the third dielectric material 145 in between. The first and the second capacitor region C1 and C2 are laterally separated from each other by a region D, for example. In this case, the first to fourth contact electrode as well as the first to third dielectric material may be formed as layers as is shown in FIG. 14. Alternatively, a coaxial arrangement of the contact electrodes 110, 120, 130, 140 and of the dielectric layers may be selected. In the coaxial arrangement, the first contact electrode 110, for example, might form a central line around which the other layers might be arranged. In this case, FIG. 14 would be a radial cross-sectional view in which the radius r=0 would be in the contact layer 110. It is also possible that the fourth contact electrode 140 forms the central line, i. e. r=0 would then be in the fourth contact electrode 140.

In the side view of FIG. 14, all hatched components are therefore made of an electrically insulating material for which ceramic or plastic plates, printed circuit boards or similar materials may be used. The non-hatched elements are made of an electrically conductive material having a high conductivity such as copper or are formed by semiconductor boards. At the second measuring signal output 124, a current can be measured as a second capacitive measuring signal, for example, through the electric field, and at the first measuring signal output 122, a voltage as the first capacitive measuring signal can be measured through the electric field strength. Between the current path output 114 and the reference terminal 144, e. g. a load 150 may be connected, which may include a piezoelectric motor, a piezoelectric oscillator or other treatment components. Between the current path input 112 and the reference terminal 144, e. g. a power supply unit (current or voltage source) may be connected.

Various embodiments of the purely capacitive sensor will be explained hereafter with reference to FIGS. 15A through 15E.

Figure 15A:
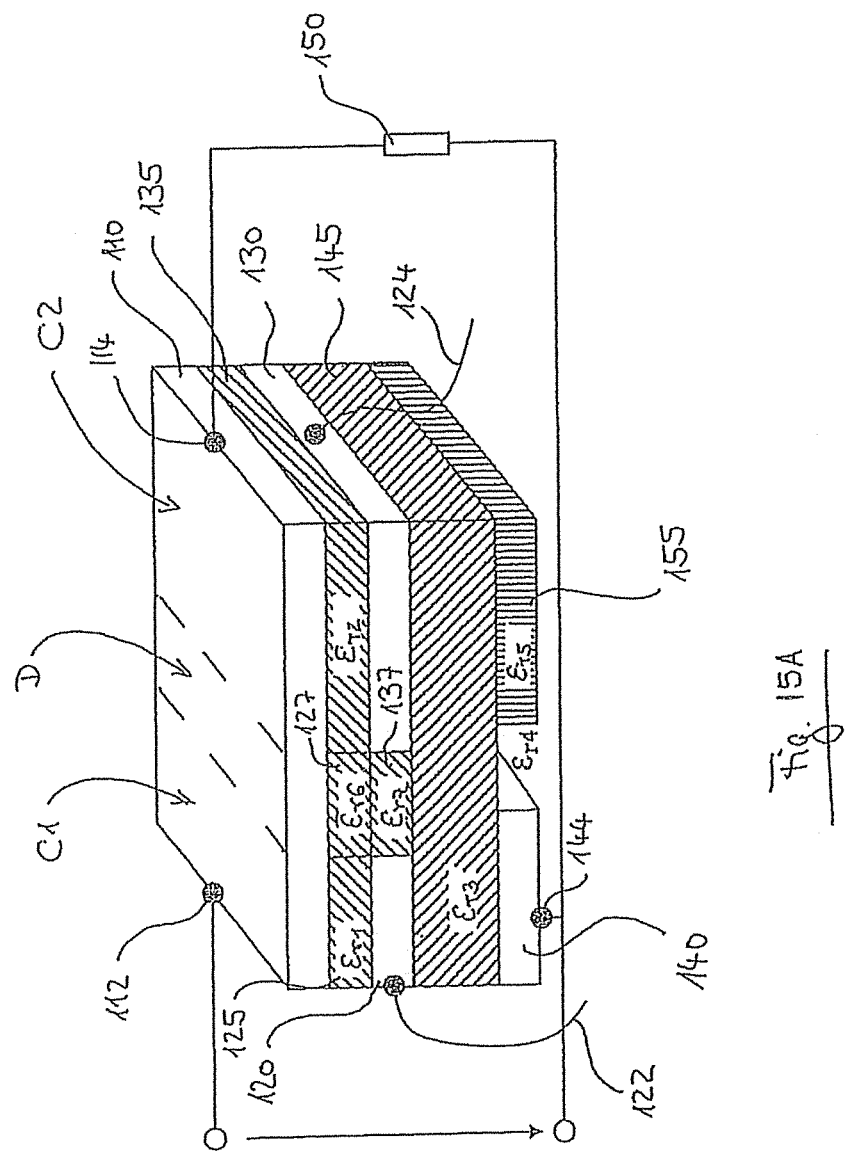

FIG. 15A illustrates a perspective view of a possible layered configuration of the treatment device, which differs from the embodiment shown in the cross-sectional view of FIG. 14 only in the fact that an intermediate dielectric material 127 is formed between the first dielectric material 125 and the second dielectric material 135. As in FIG. 14, an additional dielectric layer 137 is formed between the second contact electrode 120 and the third contact electrode 130. Finally, a fifth dielectric layer 155 is formed on a side of the third dielectric layer 145, which is opposite the third contact electrode 130, and a dielectric interface (made of air, for example) is formed between the fourth contact electrode 140 and the fifth dielectric layer 155.

All dielectric layers may have different relative dielectric constants so that the first dielectric material 125 has a first relative dielectric constant $\in_{r1}$, the second dielectric material 135 has a second relative dielectric constant $\in_{r2}$, the third dielectric material 145 has a third relative dielectric constant $\in_{r2}$, the dielectric interface has a fourth relative dielectric constant $\in_{r4}$, the fifth dielectric layer 155 has a fifth relative dielectric constant $\in_{r5}$, the intermediate dielectric material 127 has a sixth relative dielectric constant $\in_{r6}$ and the additional dielectric layer 137 has a seventh relative dielectric constant $\in_{r7}$. In further embodiments, the dielectric constants ($\in_{r1}, \in_{r2}, \in_{r3}, \in_{r4}, \in_{r5}, \in_{r6}, \in_{r7}$) mentioned above are intentionally selected different or some of them are selected equal to each other (e. g. by selecting the same material). The fifth relative dielectric constant $\in_{r5}$, for example, may be selected in such a way that interference capacitances in relation to a substrate lying underneath (which may also have the fourth relative dielectric constant $\in_{r4}$) or in relation to other components are avoided.

The first capacitance C1 in the first capacitor region differs from the second capacitance C2 in the second capacitor region especially in the event that the relevant first capacitor area differs from the second capacitor area, but also in the event that the relative dielectric constants ($\epsilon_{r1}$, $\epsilon_{r2}$) or the layer thicknesses of the dielectric layers 125, 135 were selected different.

The load 150 is connected again between the current path output 114 and the reference terminal 144. Similarly, the supply source is connected between the current path input 112 and the reference terminal 144 (as is indicated by the arrow). In further embodiments, it is also possible to arrange the current path input 112 and the current path output 114 along the first contact electrode 110 in other positions than the positions shown. Specifically, the current path input 112 and/or the current path output 114 may also be arranged in the region D. In addition, they may have a minimum distance from each other.

The values of the material and the geometric dimensions may be selected, for example, in such a way that the values of the first capacitance C1, the second capacitance C2 and the third capacitance C3 are within the pico- and nanofarad ranges. To that end, the materials may be selected appropriately and the geometric dimensions may also be varied appropriately and, in addition to the thickness of each layer (in particular of the dielectric layers), the lateral extensions of the contact electrodes (e. g. the areas of the capacitor faces) primarily influence the capacitance of the capacitors.

Further, the selected capacitance values may depend on whether the capacitive sensor is to be inserted into the power supply unit and/or into the hand-piece or whether a separate acquisition of the measured values is carried out. For measuring a voltage within the power supply unit, for example, the geometric dimensions (e. g. capacitor region C1) may be 30 mm×22 mm×0.7 mm and the capacitance values may be ~160 pF for C1=C3 and ~80 pF for C13. Here, all values are rounded values so that deviations of ±10% or ±50% are possible. For a current measurement within the power supply unit, geometric dimensions (e. g. for the capacitor region C2) of 30 mm×20 mm×0.3 mm and a capacitance value of ~160 pF for C2 may be used, for example.

In a capacitive measurement within the hand-piece, geometric dimensions of 3 mm×2.2 mm×0.7 mm and capacitance values of ~16 pF for C1=C3 and ~8 pF for C13 may be used for the voltage measurement, for example. For a current measurement by the capacitive sensor within the hand-piece, geometric dimensions of 3.0 mm×2.0 mm×0.3 mm and a capacitance value of ~16 pF for C2 may be used, for example.

Figure 15B:
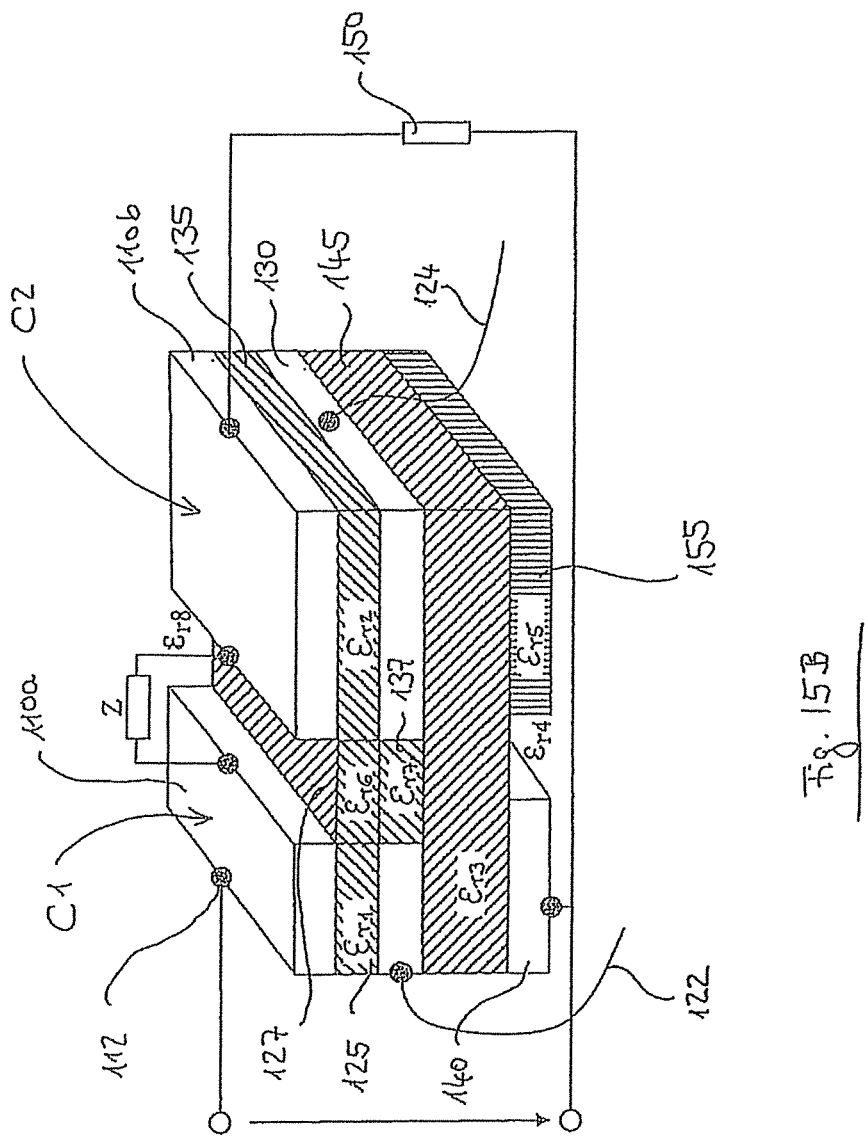

FIG. 15B illustrates another perspective view of another embodiment which differs from the embodiment shown in FIG. 15A in that the first contact electrode 110 includes a first portion 110a and a second portion 110b, the first portion 110a and the second portion 110b being electrically intercoupled through an impedance Z. In addition, between the first portion 110a and the second portion 110b of the first contact electrode 110, a dielectric medium having an eighth relative dielectric constant $\epsilon_{r8}$ is formed, which may be an air interface, for example. All other layers are formed in the same way as in the embodiment shown in FIG. 15A so that the description is not repeated here.

Figure 15C:
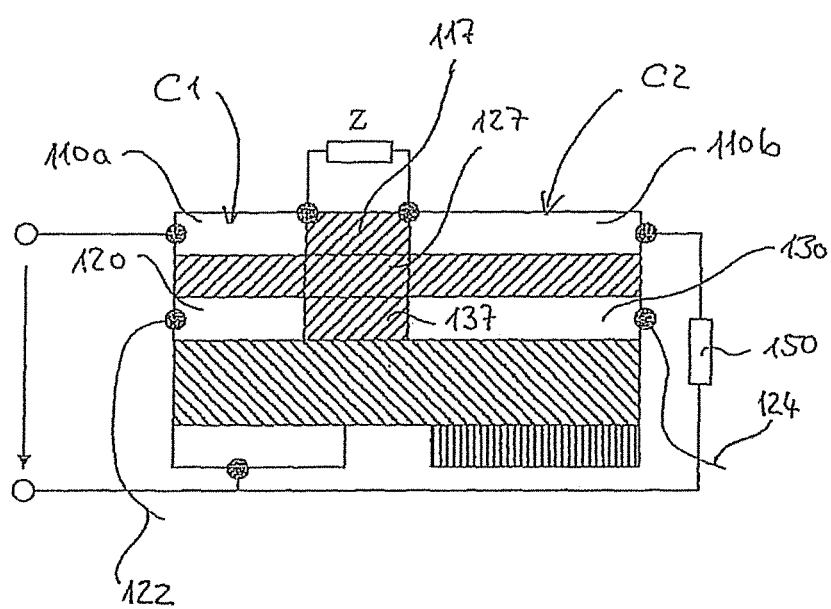

FIG. 15C illustrates a further embodiment in a cross-sectional view along a cutting plane similarly to that selected in FIG. 14 (in parallel to the current path). Similarly to the embodiment shown in FIG. 15B, in the embodiment of FIG. 15C, the first contact electrode 110 includes a first portion 110a and a second portion 110b so that the first portion 110a forms together with the second contact electrode 120, which is isolated by the first dielectric material 125, the first capacitance C1, and the second capacitance C2 is formed by the second portion 110b and the third contact electrode 130 which are electrically isolated from each other by the second dielectric material 135. Similarly to the embodiment shown in FIG. 15B, the first and the second portion 110a, 110b of the first contact electrode 110 are electrically interconnected through an impedance Z. However, in this embodiment, an additional dielectric layer 117, which has e. g. an eighth relative dielectric constant $\epsilon_{r8}$, is formed between the first portion 110a and the second portion 110b. In the embodiment shown in FIG. 15C, the additional dielectric layer 117, the intermediate dielectric material 127 and the additional dielectric layer 137 are therefore stacked on top of one another. The impedance Z shown in FIGS. 15B and 15C may be an impedance of an electric line, for example, which interconnects the two contact electrodes, or it may intentionally be a passive component (a capacitance and/or an inductance) which has a predetermined value for the impedance, which is considered again when the measuring signals are detected and the subsequent control (e. g. of the relative phase) is carried out. In embodiments, the value of the impedance Z is, for example, selected to intentionally change the input signal. This is to provide a coarse tuning, for example, and fine tuning is done in the control process.

The layer configurations as they are shown in FIGS. 14 through 15C are only examples and the elements/layers may be also arranged in relation to each other in another way. FIG. 15D illustrates another embodiment in which all layers are stacked on top of one another as a stack of layers. Therefore, in the embodiment shown, the forth contact electrode 140 is formed as the bottom layer on which the third dielectric material 145 and then the second contact electrode 120 are formed. At the second contact electrode 120, the first measuring signal output 122 is, in turn, formed. On the second contact electrode 120, the first dielectric material 125 is subsequently formed on which, in turn, is formed the first portion 110a of the first contact electrode 110. The first portion 110a includes the current path input 112 which is connected to a power supply source, for example. On the first portion 110a of the first contact electrode 110, the additional dielectric layer 117 and then the second portion 110b of the first contact electrode 110 are formed.

Therefore, similar to FIG. 15C, the first and the second portion 110a and 110b of the first contact electrode 110 are electrically isolated from each other by the additional dielectric layer 117, the layers not being arranged adjacent to each other as shown in FIG. 15C but being arranged as a stack of layers on top of one other. Similarly to FIG. 15B and FIG. 15C, the first portion and the second portion 110a, 110b are electrically interconnected through an impedance Z. On the second portion 110b, the second dielectric material 135 is subsequently formed and, finally, the third contact electrode 130 is arranged as the last layer in the stack of layers of FIG. 15D. The third contact electrode 130 includes, in turn, the second measuring signal output 124 from which the second measuring signal can be picked off and which is not arranged in the marginal region in this embodiment but contacts the third contact electrode 130 substantially in the center.

As is shown in FIG. 15D, the layers in the stack of layers may all have the same lateral extension (surface area). However, a pyramid- or cone-like configuration may also be selected, in which some of the contact electrodes 110 through 140 have different surface areas so that the capacitance values between the respective contact electrodes can be intentionally selected. Similarly to the other embodiments, the load 150 is electrically connected between the current path output 114 at the second portion 110b of the first contact electrode 110 and the reference terminal 144 connected to the fourth contact electrode 140.

Figure 15E:
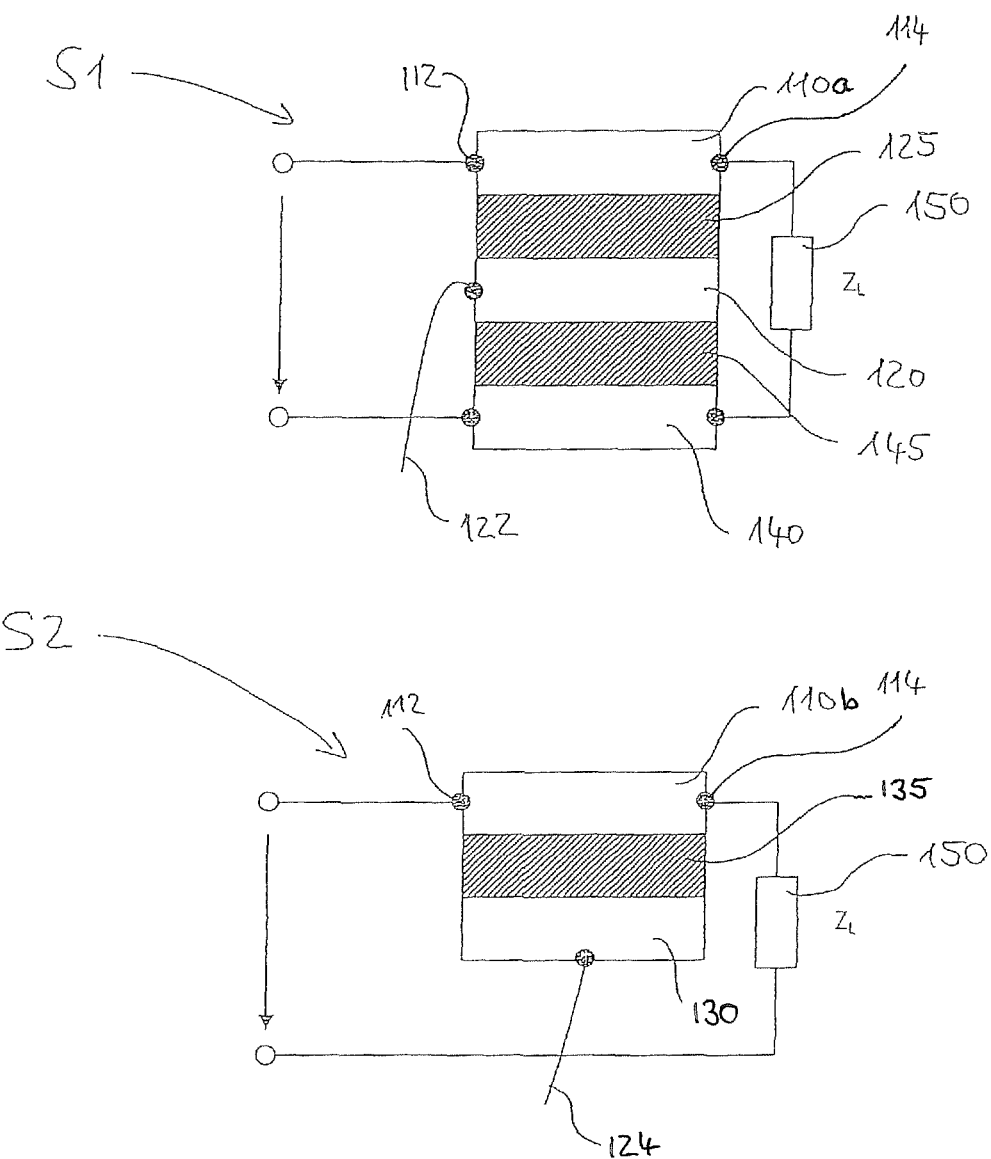

FIG. 15E illustrates an embodiment in which the layer structure including the first portion 110a of the first contact electrode 110, the first dielectric material 125, the second contact electrode 120, the third dielectric material 145 and the fourth contact electrode 140 forms a first sensor unit S1. A second sensor unit S2 is then formed by the second portion 110b of the first contact electrode 110, the second dielectric material 135 and the third contact electrode 130, all contact electrodes and dielectric layers being stacked as layers on top of one another as it is shown in the embodiments described above. In this embodiment, the two sensors S1 and S2 detect the first and the second measuring signal in a physically separated manner. One of the two sensors S1, S2 may be arranged in the hand-piece of the treatment device or in the connecting line, for example, whereas the other of the two sensors S1, S2 is accordingly arranged either in the connecting line or in the power supply unit. Embodiments include therefore the following options. The first sensor unit S1 is arranged in the hand-piece, whereas the second sensor unit S2 is arranged in the connecting line or in the power supply unit. In another embodiment, the first sensor unit S1 is arranged in the connecting line, whereas the second sensor unit S2 is arranged in the hand-piece or in the power supply unit.

In another embodiment, the first sensor unit S1 is arranged in the power supply unit, whereas the second sensor unit S2 is arranged in the hand-piece or in the connecting line. Therefore, embodiments also include cases in which the first and the second sensor unit S1, S2 are arranged together on the primary side or are arranged together on the secondary side. In further embodiments, the first sensor unit S1 is arranged on the primary side and the second sensor unit S2 is arranged on the secondary side. Conversely, the second sensor unit S2 may be arranged on the primary side and the first sensor unit S1 may be arranged on the secondary side. In addition, in further embodiments, the first and the second sensor unit S1, S2 may be arranged together in the hand-piece or together in the power supply unit or together in the connecting line.

The capacitive measuring signal at the first measuring signal output 122 may be supplied to a control unit, for example, which is not in direct contact with the power power supply unit of the treatment device but only controls the power supply unit through a control signal. If they are implemented as individual components, they sense a measurand such as a current or a voltage or a relative phase between a current signal and a voltage signal.

Therefore, the embodiment of FIG. 15E represents a case in which the region D as it is shown in FIG. 14 or FIG. 15B is selected large enough to physically separate the first capacitance C1 and the second capacitance C2 from each other. Alternatively, the device shown is separated in the region D (see FIG. 15A, for example) and the two portions are spaced apart from each other and are electrically contacted.

The electrical connection of the load 150 is made in the same way as in the embodiments described above by connecting the load 150 between the first portion 110a and the fourth contact electrode 140, on the one hand, and by contacting it to the second portion 110b of the first contact electrode 110, on the other.

In all configurations as they are shown in FIGS. 15A through 15E, the layers may be successively deposited in a manufacturing method using thin-film technology.

Therefore, embodiments include also a sensor which only senses a capacitive measuring signal without including other impedance means or induction elements or other capacitive sensors. Therefore, one sensor, namely S2 as it is shown in FIG. 15E, represents also an embodiment of the present invention.

Figure 16A:
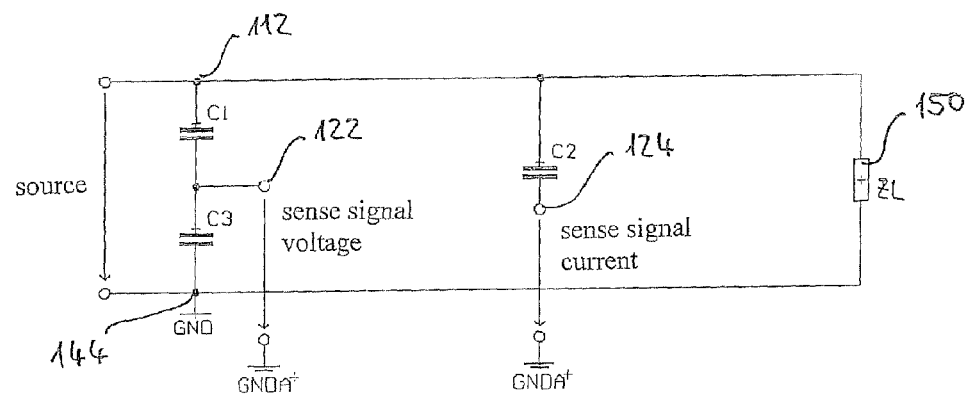
FIGS. 16A-G illustrate circuit diagrams showing how the first and the second capacitive measuring signals are detected in embodiments.
Figure 16B:
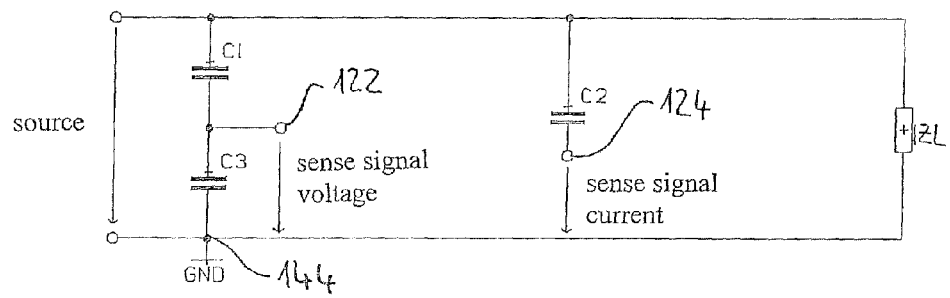
Figure 16C:
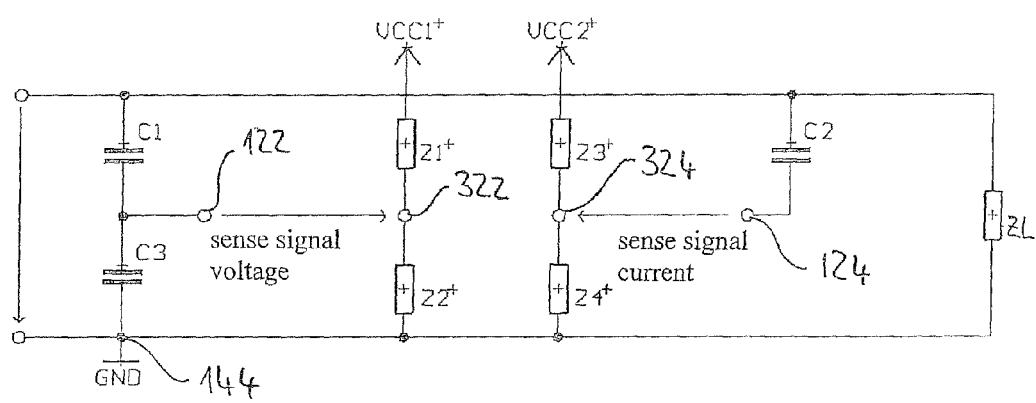

FIGS. 16A through 16C show possible circuit diagrams for sensing the first and the second measuring signal for purely capacitive sensors.

FIG. 16A shows a first circuit option in which the first capacitor C1 and the third capacitor C3 are connected in series between the current path input 112 and the reference terminal 144. The first measuring signal output 122 is connected between the first capacitor C1 and the third capacitor C3. The second capacitor C2 is connected between the current path input 112 (or the current path output 114) and a second measuring signal output 124. The load 150 has an ohmic resistance RL or an impedance ZL and is also connected between the current path input 112 and the reference terminal 144. The first measuring signal can be picked off between the first measuring signal output 122 and an additional reference potential GNDA and the second measuring signal can be picked off between the second measuring signal output 124 and the additional reference potential GNDA. Therefore, in the embodiment shown in FIG. 16A, the first and the second measuring signal are related to a common reference potential which is equal to or different from the ground potential GND. For example, the first measuring signal may be used for the voltage measurement and the second measuring signal may be used for the current measurement.

FIG. 16B shows an alternative circuit configuration in which the additional reference potential GNDA is equal to the ground potential GND so that the first measuring signal can be picked off between the first measuring signal output and the reference terminal 144 and the second measuring signal can be picked off between the second measuring signal output 124 and the reference terminal 144.

FIG. 16C shows a further embodiment in which a first impedance Z1 and a second impedance Z2 are connected in series between a first reference voltage VCC1 and the reference terminal 144 and, in addition, a third impedance Z3 and a fourth impedance Z4 are connected in series between a second reference voltage VCC2 and the reference terminal 144. In the embodiment shown in FIG. 16C, the first measuring signal is picked off between the first measuring signal output 122 and a first reference point 322 located between the first impedance Z1 and the second impedance Z2. The second measuring signal is measured between the second measuring signal output 124 and a second reference point 324 located between the third impedance Z3 and the fourth impedance Z4. The first through fourth impedance Z1 through Z4 may be, for example, simple ohmic resistances or may be other passive components such as capacitors and/or inductors. It is also possible that the first reference voltage VCC1 and the second reference voltage VCC2 are different or have the same voltage value. Therefore, the first through fourth impedance Z1 through Z4 represent additional reference points for the current or voltage measurement, which in particular allow a more exact signal processing. The first measuring signal may include a measured voltage and the second measuring signal may include a measured current.

Figure 16D:
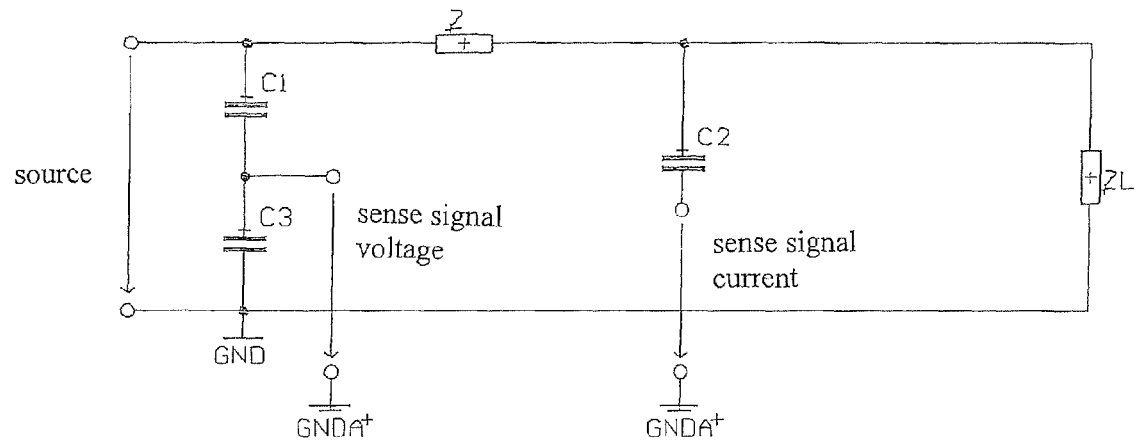

FIG. 16D shows a fourth circuit option which differs from the first circuit option (see FIG. 16A) in that the electrical connection between the first capacitor C1 and the second capacitor C2 has an impedance Z and hence corresponds to the case as it is shown in FIGS. 15B, 15C and 15D, for example. All other components of the fourth circuit option correspond to the first circuit option of FIG. 16A so that the description is not repeated here.

Figure 16E:
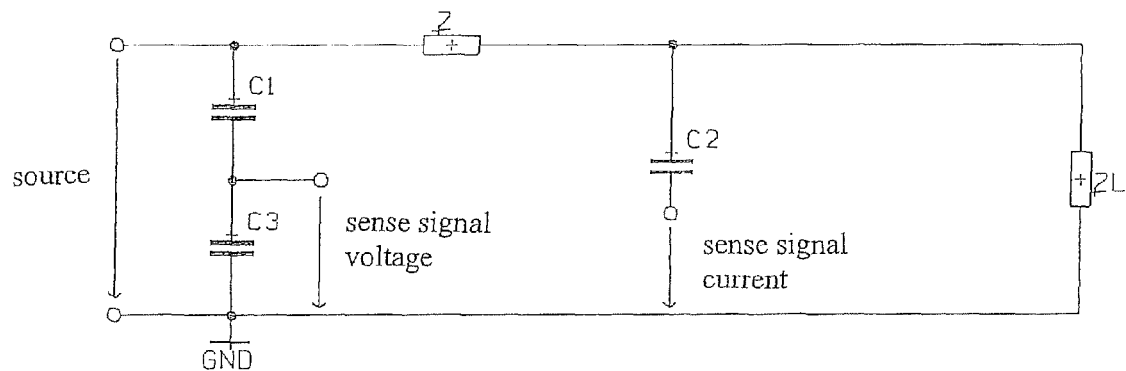

FIG. 16E shows a fifth circuit option which differs from the second circuit option (see FIG. 16B) in that the impedance Z is connected between the first capacitor C1 and the second capacitor C2 (similarly to FIG. 16D).

Figure 16F:
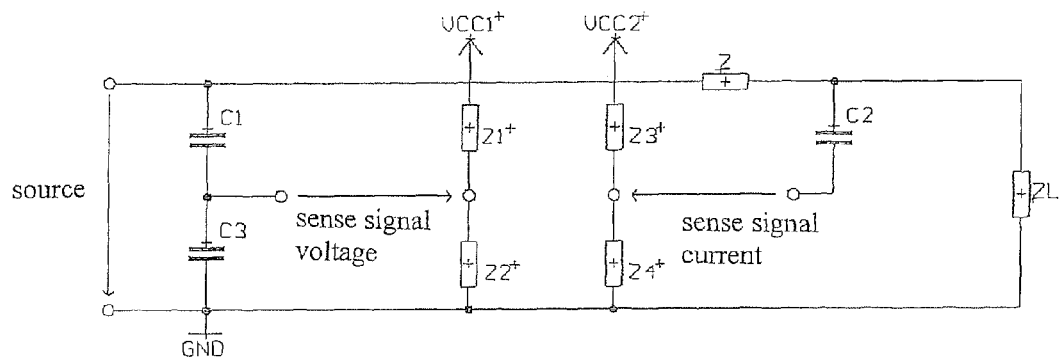

FIG. 16F shows a sixth circuit option which differs from the third circuit option (see FIG. 16C) only in that the impedance Z is connected between the first capacitor C1 and the second capacitor C2. All other components of the embodiment of FIG. 16F correspond to the third circuit option (see FIG. 16C) so that the description is not repeated here.

Figure 16G:
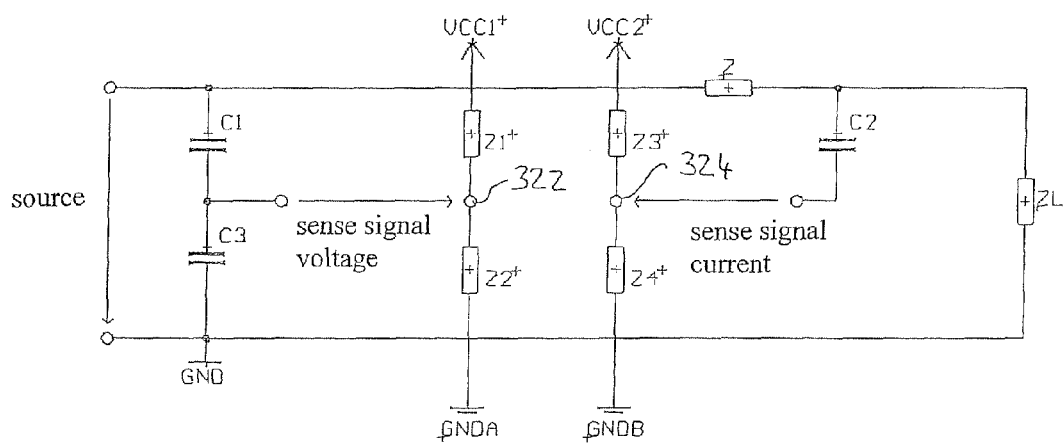

FIG. 16G shows a further embodiment which differs from the embodiment shown in FIG. 16F in that the second impedance Z2 is arranged between the first reference point 322 and a first reference potential GNDA. In addition, the fourth impedance Z4 in the embodiment shown in FIG. 16G is arranged between the second reference point 324 and the second reference potential GNDB. The first reference potential GNDA and the second reference potential GNDB may be different from the reference potential GND, for example, and the second reference potential GNDB may be equal to or different from the first reference potential GNDA. All other features of the embodiment shown in FIG. 16G correspond to those in the embodiment shown in FIG. 16F or those in the embodiment shown in FIG. 16C so that the description is not repeated here. Therefore, the seventh circuit option of FIG. 16G shows the use of different reference points for the exemplary current and voltage measurements.

The load 150 has a load impedance ZL which may have both an ohmic portion (ohmic resistance) and a capacitive and/or an inductive portion, for example. It may also have only an ohmic resistance. The impedance Z may also have an ohmic resistance and/or a capacitive and/or an inductive portion.

The Figures described below relate again to the more general case that the impedance means may comprise at least one of an additional capacitor and an induction element.

Figure 17:
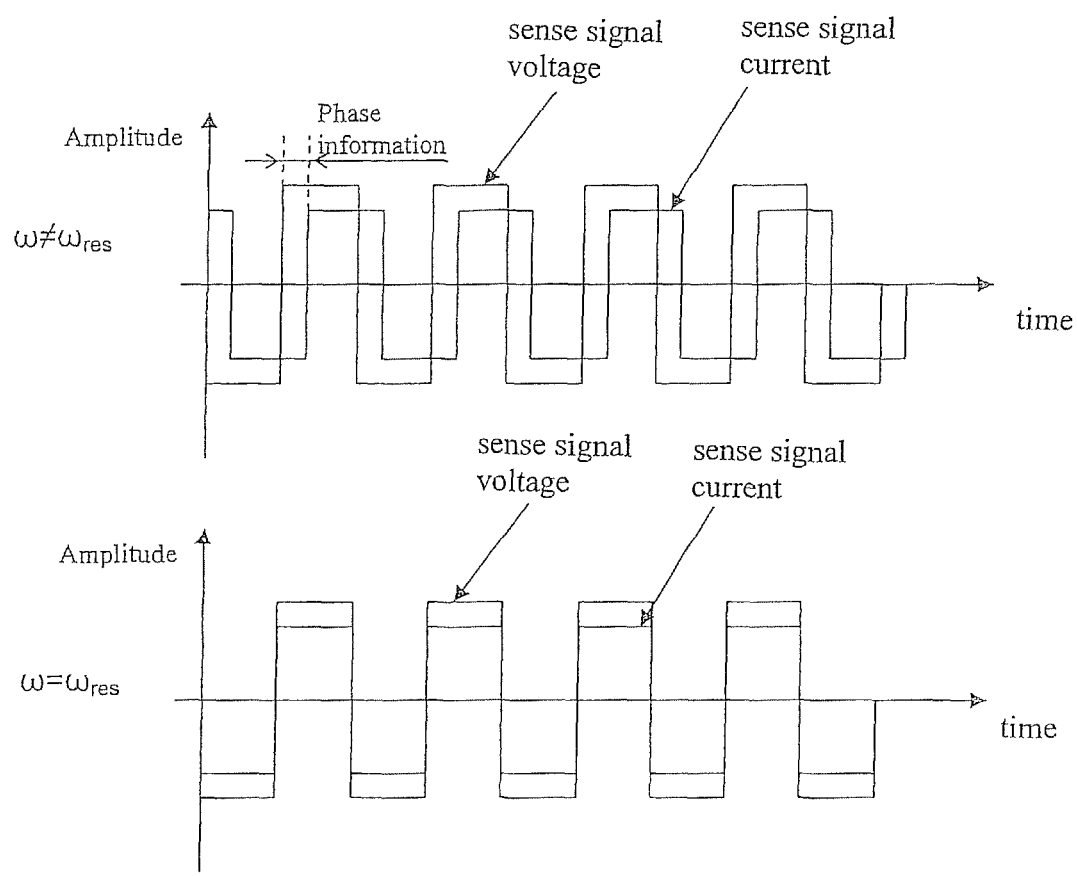

FIG. 17 shows a possible signal curve for the voltage measuring signal and the current measuring signal, as function of time. In the case shown at the top, no resonance occurs ($f \neq f_{RES}$) and in the case shown below, a resonance occurs ($f=f_{RES}$). As appears from the FIG. 17, both the voltage and the current signal in the case of resonance is formed in such a way that they have the same frequency and have no relative phase shift (they are in phase). However, away from the resonance point, a phase shift occurs between the voltage measuring signal and the current measuring signal, which is shown at the top of FIG. 17. The phase information shown represents the phase shift between the voltage measuring signal and the current measuring signal. Conversely, the phase shift shown in FIG. 17 results in leaving the resonance points (discord). In the embodiment shown in FIG. 17, the amplitude of the voltage measuring signal is higher than that of the current measuring signal, which, however, only serves an improved representation and may be different in further embodiments. In addition, rectangular pulses are shown in an idealized form in FIG. 17 and these pulses may also be harmonic vibrations in the form of sinusoidal or cosinoidal vibrations.

The result of the phase shift as it is shown at the top of FIG. 17 is that the voltage measuring signal runs behind the current measuring signal and hence a piezoelectric element (e. g. a piezoelectric motor) does not operate at resonance. This causes additional losses, which the present invention intends to avoid. If the system is not at resonance ($f \neq f_{RES}$), a control offset occurs which appears in the form of the phase information shown. The signal shape which is shown in the idealized form in FIG. 17 changes according to the hardware-related control configuration. The signal shape may significantly change during the control operation, depending on how the electric circuit was designed or how the piezoelectric motor was mechanically loaded.

In the resonance case ($f=F_{RES}$), the load 150 to be driven, that is, the piezoelectric motor as well as portions of the electronic driving circuits, for example, is in an almost ideally resistive state (current and voltage signals have the same phase—no phase shift). This results in current peaks and voltage peaks which may easily be sensed by means of the capacitive sensors as they are described by the present invention. The measuring signals (current and voltage, for example) may be fed as controlled or regulated quantities into the closed control loop. The effective values of these signals are primarily determined by the geometry or the materials of the capacitive sensors (see also FIGS. 14 and 15).

However, the sensors as they are defined by the present invention do not only allow to find an optimum operating frequency (resonance) but also to determine the curves of the current and voltage signals relatively accurately in order to detect the power appropriately accurately. This effects an optimization of the electronic system (efficiency) and, at the same time, an optimization of the mechanical output at the piezoelectric tip of the exemplary dental hand-piece.

Figure 18:
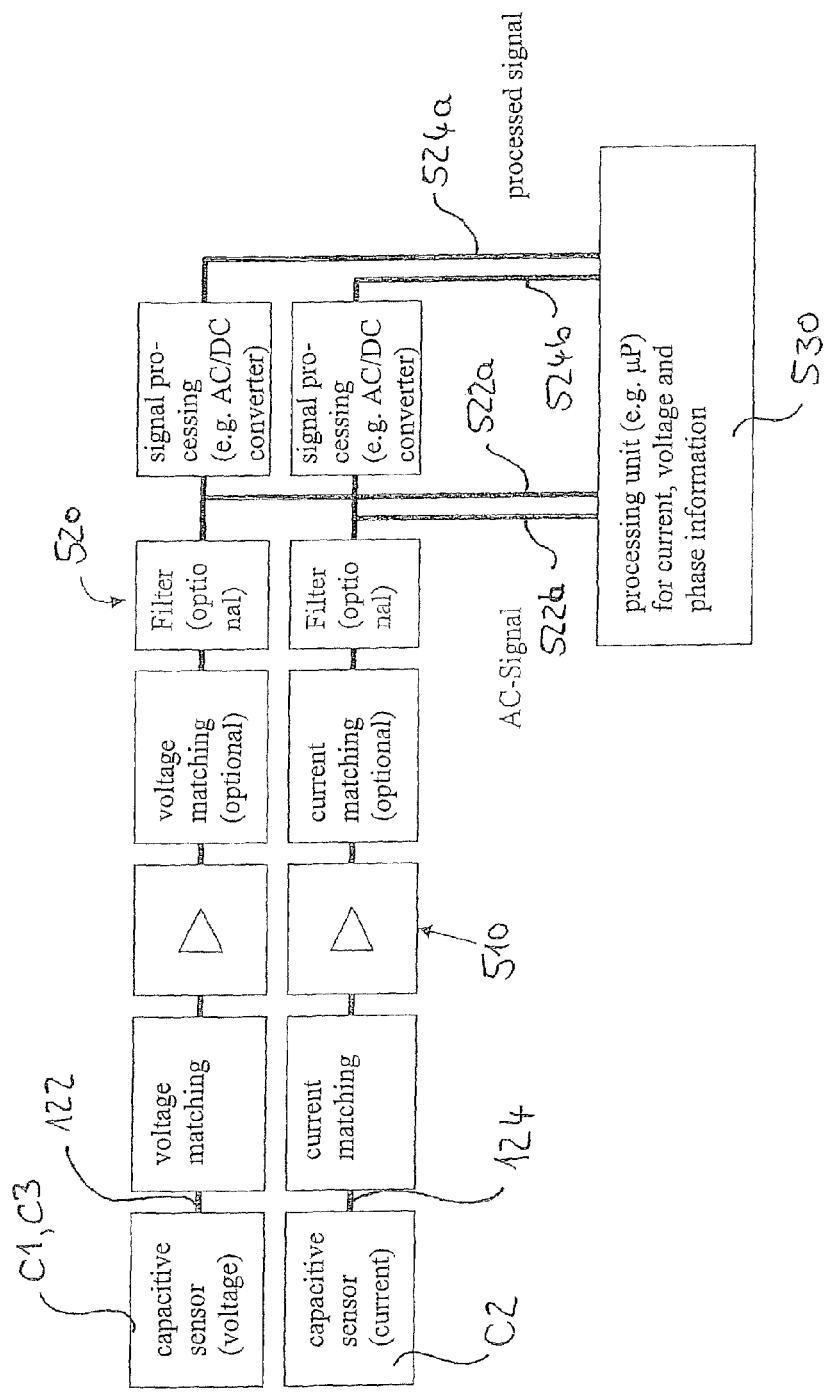
FIG. 18 illustrates a signal processing operation for a voltage and a current signal.

FIG. 18 exemplarily shows a possible evaluation of the first and the second measuring signal. In the example shown, a signal for voltage detection is capacitively picked off from the first measuring signal output 122 and a signal for current detection is capacitively picked off from the second measuring signal output 124. After the two measuring signals have been detected, the voltage is adjusted by means of the first through fourth impedance Z1 through Z4 shown in FIG. 16, for example. In the embodiment shown in FIG. 18, the two measuring signals are subsequently amplified by measuring amplifiers 510. After the amplification, another voltage adjustment may optionally be carried out and, in addition, a filter 520 which may include a high-frequency filter, for example, may be subsequently arranged to filter out high-frequent interferences. Alternatively or optionally, band-pass filters or low-pass filters may also be arranged to filter out interfering frequency ranges. On the one hand, the outputs of the two filters 520 for the two measuring signals are coupled to an evaluating unit 530, and, on the other, the signals at the filter outputs may be provided to further signal processing, which may include a conversion of the AC voltage signal into a DC voltage signal, for example. The outputs of signal processing may, in turn, be supplied as evaluated signals 524a, 524b to the evaluating unit 530. Therefore, the evaluating unit 530 obtains for the first measuring signal an AC voltage signal 522a and an evaluated signal 524a. In addition, the evaluating unit 530 obtains from the second measuring signal, in turn, an AC voltage signal 522b and an additional evaluated signal 524b. The evaluating unit 530 which may include a microprocessor, for example, determines from these signals the current signal, the voltage signal and/or the phase information.

Figure 19:
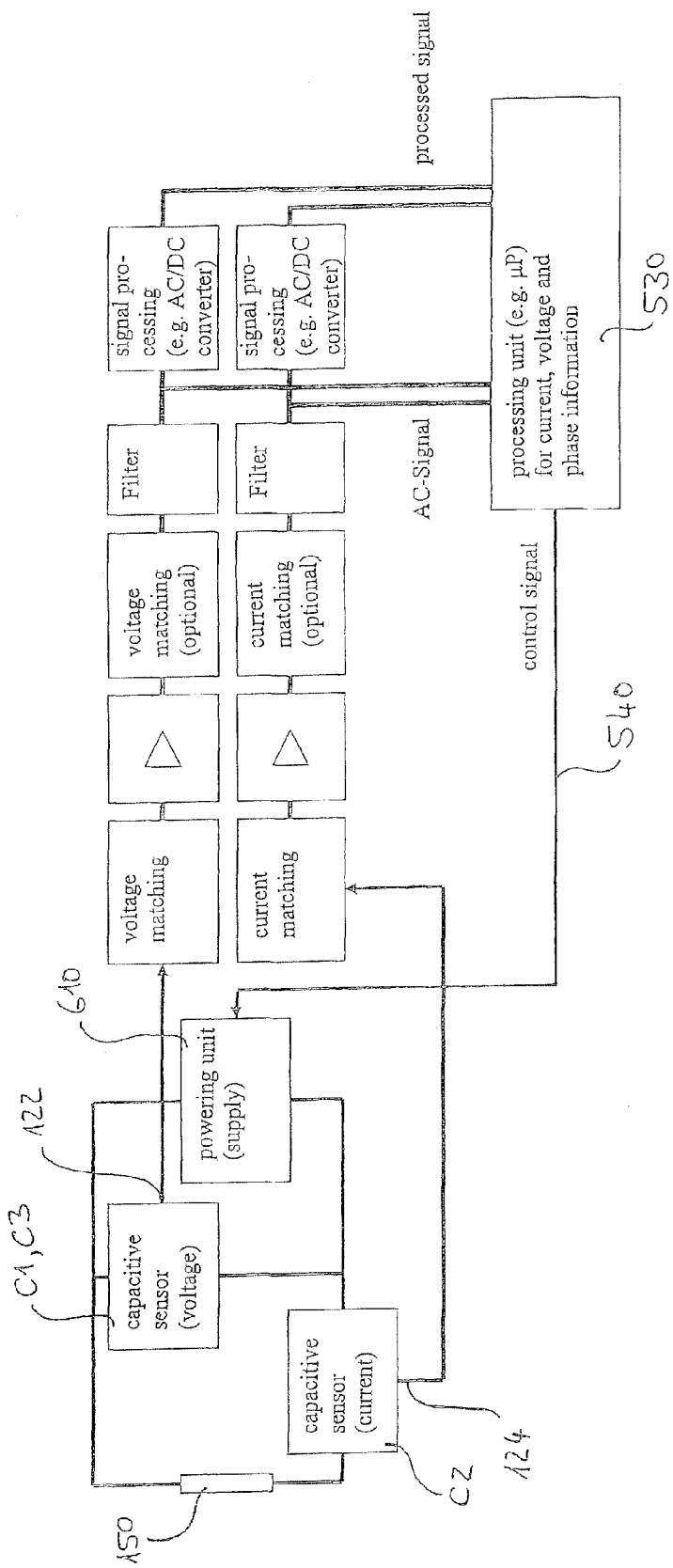
FIG. 19 illustrates a signal processing operation in the form of a closed control loop for the feedback to the power supply unit.

FIG. 19 shows an embodiment in which the signal processing unit shown in FIG. 18 is used to generate a control signal 540 by the evaluating unit 530, which is, in turn, supplied to a power supply unit 610. The power supply unit 610 may, for example, control the operating voltage and may, in response to the control signal 540, change the curve of the voltage signal in relation to the curve of the current signal (phase response) and/or may change the frequency of the voltage signal and/or current signal. Further, the embodiment of FIG. 19 shows that a first capacitive sensor, which may include the capacitors C1 and C3, for example, has the first measuring signal output 122 to provide the voltage signal to signal processing and that an additional capacitive sensor for the current includes the second capacitor C2 and supplies the current signal to the signal processing unit through the second measuring signal output 124.

The power supply unit 610 provides the current and voltage signal to the load or load impedance 150, the control signal 540 being provided by the evaluating unit in such a way that, on the one hand, the load impedance 150 operates at resonance if possible and, on the other, the efficiency is optimized (by controlling the power input). Therefore, the integration of the capacitive sensor and the signal processing unit for the measuring signals in a control loop is shown in FIG. 19, the load impedance 150 being preferably configured as a piezoelectric drive for a scaler.

Although capacitive sensors are shown in FIGS. 18 and 19, the signal detection shown can also be applied to the case of general impedance means (i. e. the capacitive sensor may also be configured as an induction element and the capacitive signal may also be an inductive signal without departing from the illustrated principle of detection).

Figure 20:
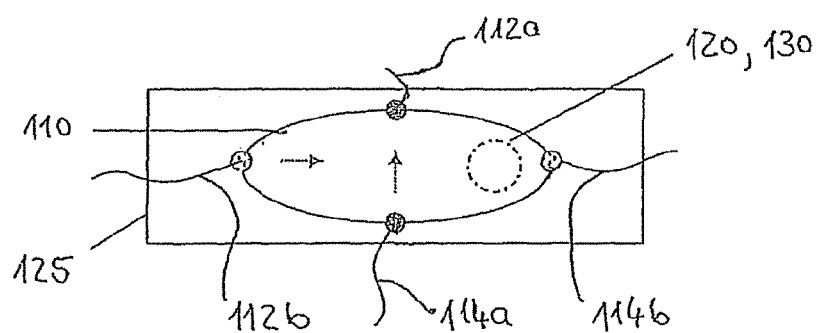
FIG. 20 illustrates a top view of the medical treatment device having different supply points.

FIG. 20 illustrates a further embodiment of the present invention, in which the supply points, i. e. the current path input 112 and the current path output 114 on the first contact electrode 110, are varied. In the particular case, a top view on the cross-sectional view shown in FIG. 14 can be seen here, a horizontal and a vertical supply being shown as examples of different geometries in the two-dimensional space. In the embodiment shown in FIG. 20, the first contact electrode 110 is formed as an elliptical disc deposited on the first dielectric material 125. The elliptical first contact electrode 110 has a major axis and a minor axis. In the case of a vertical supply, the supply is carried out (substantially) along the minor axis (112a, 114a), whereas in case of a horizontal supply, the current path input 112b and the current path output 114b are (substantially) formed along the major axis. In this case, the supply points may vary by ±20° around the major or minor axis or may be formed along different axes (e. g. the current path input 112 may be formed along the major axis and the current path output 114 may be formed along the minor axis).

In FIG. 20, a second or third contact electrode 120, 130 arranged below the first dielectric material 125 is represented only schematically. The variation of the supply points results in that high frequency portions in the electric input signal can be detected, as at very high frequency portions, the flowthrough of the first contact electrode 110 by charge carriers is delayed and hence a time-variable capacitive measuring signal is generated. This allows to optimize the medical treatment device, for example, to the effect that the input signal is as harmonic as possible, by detecting interfering high-frequent harmonic waves (which are produced by transient signals, for example) and by suppressing them. To that end, the first contact electrode may have a total of four supply points, for example, which are used in parallel or alternately to detect high-frequent harmonic waves by comparing the supply and discharge at different points and to cause, in response to the detected harmonic waves, a feedback to the power supply unit 610 through the evaluating unit 530 to the effect that the high-frequent harmonic waves are minimized.

Figure 21:
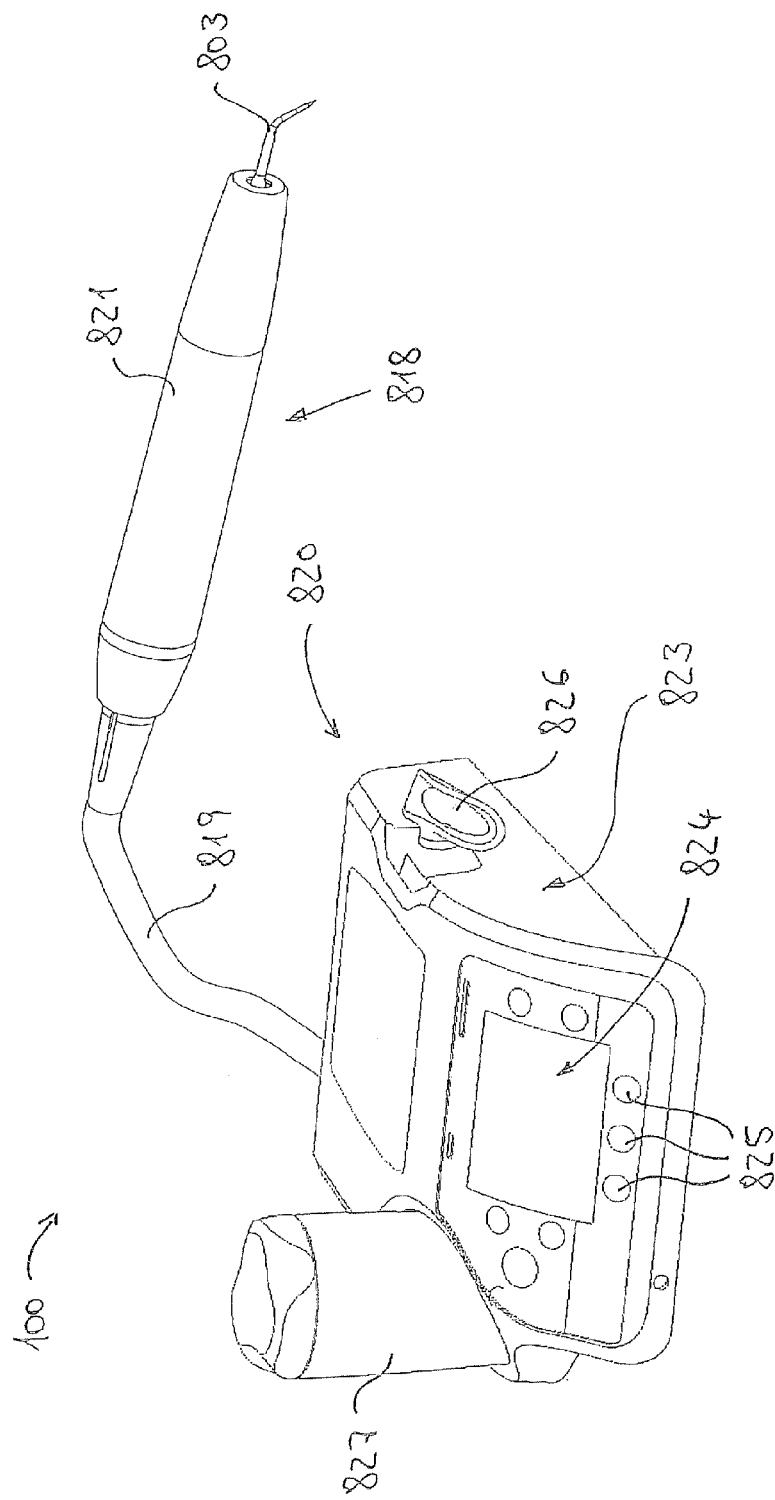
FIG. 21 illustrates an embodiment of a medical, in particular dental, treatment device having a hand-piece for scaling.

FIG. 21 shows the medical, in particular dental, treatment device 100 which is configured as a scaling treatment device. It comprises, for example, a handle element or hand-piece 818; a control device 820; and a supply or connecting tube 819 connecting the control device 820 to the hand-piece 818.

The straight elongated hand-piece 818 includes a cylindrical hollow outer casing 821, in which, amongst other things, a driving unit for a tool 803 connectable to the hand-piece 818 is arranged. The control device 820 includes a housing 823 having a display 824 for fixed or adjustable operating parameters. In addition, a plurality of control elements 825, such as a push button, for selecting or changing the output parameters as well as a hand-piece holder 826 and a liquid source 827 for a coolant or a scavenging liquid are provided.

The supply or connecting tube 819 contains, for example, a plurality of media or service fluid lines, in particular electric lines connecting the drive unit to the relevant power sources.

The sensors as they are shown in FIG. 1, 2 or 14, for example, may be accommodated in the hand-piece 818, the control device 820 or the supply line 819 and may therefore form the medical treatment device according to the invention.

Therefore, embodiments of the present invention include sensors for a separated or combined detection of current and voltage and may be summarized as follows. For example, the principle of a plate capacitor which may be implemented two- or three-dimensionally and includes a PCB (printed circuit board), for example, is used to detect two of the current and voltage quantities. Materials of the type FR4, ceramic substrates with printed insulating and conductive patterns, sheet structures or coaxial arrangements may be used as the materials. A special feature of capacitive sensors as they are used in embodiments of the present invention is that these sensors allow a simple, fail-safe and low-cost integration into existing components. They may be formed as electronic PCBs (two-dimensional structures) or may be accommodated in lines to the application unit, such as a cable (three-dimensional structure), for example. Another feature of these sensors is that they can be flexibly adapted to the respective measuring function by selecting the geometries of the structures (e. g. area dimensions or laminations). In addition, in dependence on the supply and discharge points and on the detection points, the distribution of charge density in the stationary case as well as a change in this distribution of charge density in the dynamic case can be determined. Therefore, embodiments allow a combination of current and voltage measurements in one sensor (having a multilayer structure) or a separated measurement of current and voltage by appropriately configuring and selecting the supply points, discharge points and detection points for the measurands. As the measurands, the amplitude, phase and signal curve of the voltage signal and of the current signal, for example, may be used. It is also possible to achieve an adaptation to the measuring function by the material of the electrically conductive and insulating structures by appropriately directing the electric flux lines, for example. This is relevant both to the physical size of the device and the immunity to interference (e. g. the destruction of interference capacitances), amongst others. In addition, it is possible to effect a passive or active screening.

As shown above, a separated arrangement of the sensors (e. g. as inductive and capacitive sensors) is also possible. For example, respective two-plate configurations may form a capacitive sensor providing a capacitive coupling and respective two-coil configurations may define an inductive sensor providing an inductive coupling. A two-plate configuration (a capacitive sensor) may be combined with a two-coil configuration (an inductive sensor) or they may be separated from each other. Multiple combinations, in which a plurality of the capacitive or inductive sensors shown is interconnected, are also possible. The geometries of the coils and capacitive plates may differ from each other. According to the overall geometry of the planar coils, the winding number may be relatively low. It may be useful, for example, to select a PCB geometry for the planar coil, which results from the operating frequency which may include very low or very high frequencies (e. g. several 10 kHz or up to several 100 MHz). Coils having ferrite cores, which are mounted on the printed circuit board, may be primarily used at low frequencies (e. g. a few Hertzes to several 100 kHz), depending on inductance.

Optionally, one or more dielectric layers may be formed as a sheet and the electrodes may be a printed or deposited conductive material. The sensor may be implemented as a stack of layers consisting of layers stacked on top of one another, the layers in the stack of layers all having the same lateral extension (area). However, a pyramid- or cone-like configuration may also be selected, in which some of the planar electrodes 110, 120 and/or the induction element 130, for example, have different areas so that the capacitance between the planar electrodes can be intentionally selected. The primary and/or secondary plates can be optionally implemented also as conductor paths running in parallel on printed circuit boards. The induction element 130 may be configured as a coil (also as a planar coil) but may also have other components which generate an electric signal from a variable electro-magnetic field. Optionally, the inductances of the first planar electrode 110 and of the induction element 130 are firmly adjusted and are not variable. The capacitance between the first planar electrode 110 and the second planar electrode 120 is also optionally firmly adjusted and is not variable.

Further embodiments offer additional advantages. For example, the sensor may be monolithically integrated in a component using a substrate. A two-electrodes/plates configuration and a two-coil configuration may be arranged physically adjacent to each other or may be spaced apart from each other, for example. In a combined configuration, a component of the sensor is used both for the capacitive measurement and the inductive measurement. This component is arranged as a planar coil between a plate/electrode and an additional coil (secondary coil) and, on the one hand, forms together with the plate/electrode the capacitive component and, on the other, forms together with the secondary coil the inductive component. The advantage of this capacitive-inductive sensor is, among other things, the small physical size and hence the low space requirement in the treatment device. The sensor again serves the (simultaneous) detection of voltage and current.

In certain applications, one sensor portion (and therefore the measurement of either current or voltage) is sufficient to operate the treatment device.

Embodiments also include a method for controlling a load 150 of the described medical treatment device, the method comprising: detecting the capacitive measuring signal; detecting the inductive measuring signal; determining a control signal based on the capacitive measuring signal and the inductive measuring signal; and providing the control signal to a power supply unit in such a way that the control signal changes the electric input signal. In the method, the control signal may optionally be provided in such a way that the phase shift between the current signal and the voltage signal is reduced to provide a resonant operation of the load. In addition, the control signal in the method may be configured to change a real power, which is consumed by the load, in such a way that the efficiency of the treatment device increases. As a result, the method utilizes, for example, the medical treatment device as described above. Other features described with reference to the device are also utilized in the method in further embodiments.

The features of the invention, which are disclosed in the Description, Claims and Drawings, may be relevant to the realization of the invention, both individually and in any combination.

What is claimed is:

1. A medical treatment device comprising a sensor to detect operating states of a medical treatment device, the sensor comprising:
   a first electrode arranged between a current path input and a current path output, wherein an electric input signal for powering the medical treatment device is applicable to the current path input, and the current path output is configured to couple to a load of the medical treatment device;
   a second electrode separated from the first electrode by a first dielectric material, the second electrode comprising a first signal terminal for receiving a first sensor signal; and
   an impedance element separated from the first electrode by a second dielectric material, the impedance element comprising a second signal terminal for receiving a second sensor signal,
   wherein the first electrode comprises a cross section perpendicular to a direction of propagation of the electric input signal such that the first electrode and the second electrode are coupled to provide a capacitance as the first sensor signal, and wherein the impedance element is formed as a structured electrode such that the first electrode and the impedance element are coupled to provide an impedance as the second sensor signal.

2. The medical treatment device of claim 1 further comprising:
   a processing unit configured to receive the first sensor signal and the second sensor signal and based thereon to determine at least one quantity selected from a group comprising a current signal, a voltage signal, a relative phase shift and a frequency of the electric input signal.

3. The medical treatment device of claim 2, wherein the processing unit is configured to provide a control signal based on the determined at least one quantity and to provide the control signal to a power unit which is configured to generate the electric input signal, wherein the control signal is configured to cause the power unit to modify the electric input signal.

4. The medical treatment device of claim 3, wherein the processing unit is configured to provide the control signal to eliminate the relative phase shift, thereby achieving a resonant operation of the medical treatment device.

5. The medical treatment device of claim 2, wherein the processing unit is configured to modify at least one of the following: the relative phase shift between the current signal and the power signal, a frequency of the current signal and of the power signal, and a phase of the current signal and of the power signal.

6. The medical treatment device of claim 2, wherein the processing unit is configured to determine from the first sensor signal and the second sensor signal a power consumption of the load, and is configured to provide a control signal such that the at least one quantity is modified to modify the power consumption of the load.

7. The medical treatment device of claim 1, further comprising at least one device selected from:
   a hand piece with a piezo motor, a control unit for the hand piece with a piezo motor, a power line for the hand piece with a piezo motor.

8. A medical treatment device with a sensor for sensing operating states, the sensor comprising:
   a first contact electrode arranged between a current path input and a current path output, wherein an electric input signal for powering the medical treatment device is applicable to the current path input and the current path output is adapted to couple to a load of the medical treatment device;

a second contact electrode which is separated from the first contact electrode by a first dielectric layer, the second contact electrode comprising a first signal terminal for obtaining a first capacitive sensor signal;

a third contact electrode which is separated from the first contact electrode by a second dielectric material, the third contact electrode comprising a second sensor signal terminal for obtaining a second capacitive sensor signal; and a fourth contact electrode which is separated from the second contact electrode by a third dielectric material, the fourth contact electrode comprising a reference terminal for coupling to a ground potential.

9. The medical treatment device of claim 8, wherein the first and second capacitive sensor signals are measured with respect to a respective first and second reference potential.

10. The medical treatment device according to claim 8, wherein the first dielectric layer and the second dielectric layer form a common dielectric layer on which the first contact electrode is arranged on a side, and the second contact electrode and the third contact electrode are arranged laterally shifted from each other on an opposite side.

11. The medical treatment device according to claim 8, further comprising a fourth dielectric and a fifth dielectric material, wherein the fourth dielectric material separates the second contact electrode and the laterally shifted third contact electrode along a lateral region, and wherein the fifth dielectric material is arranged on the third dielectric material opposite to the third contact electrode, wherein the fourth and the fifth dielectric material are configured to suppress stray capacitances.

12. The medical treatment device of claim 8, wherein the first contact electrode comprises a first part and a second part, and wherein an impedance is arranged to electrically connect the first part with the second part.

13. A medical treatment device with a sensor for sensing operating states of a medical treatment device, the sensor comprising:

a first planar electrode arranged between a current path input and a current path output, wherein an electric input signal for powering the medical treatment device is applicable on the current path input and the current path output is configured to couple to a load of the medical treatment device;

a second planar electrode which is separated from the first planar electrode by a first dielectric material, the second planar electrode comprising a first sensor signal terminal to obtain a capacitive sensor signal; and an inductive element which is separated from the first planar electrode by a second dielectric material, the inductive element comprises a second sensor signal terminal and a third sensor signal terminal, wherein between the second sensor signal terminal and the third sensor signal terminal an inductive sensor signal is obtainable, wherein the first planar electrode comprises a cross section perpendicular to a direction of propagation of the electric input signal such that the first planar electrode and the second planar electrode comprise a capacitive coupling and the first planar electrode and the inductive element comprises an inductive coupling.

14. The medical treatment device according to claim 13, wherein the first planar electrode is arranged between the second planar electrode and the inductive element.

15. The medical treatment device of claim 13, wherein the first planar electrode is formed as a planar coil and the inductive element is formed as a further planar coil, wherein a winding number of the further planar coil is large than a winding number of the planar coil.

16. The medical treatment device according to claim 15, wherein the planar coil or the further planar coil comprise a soft magnetic coil core.

17. The medical treatment device according to claim 13, wherein the first dielectric material and the second dielectric material form a common dielectric layer and the second planar electrode and the inductive element are arranged laterally separated from each other on a side of the common dielectric layer, and wherein the first planar electrode is arranged on an opposite side of the common dielectric layer opposite to the second planar electrode and opposite to the inductive element.

18. The medical treatment device of claim 13, wherein the first planar electrode comprises a first part and a second part, wherein the first part is arranged opposite to the second planar electrode, and wherein the second part is arranged opposite to the inductive element, and wherein the first part and the second part are arranged laterally separated from each other along the common dielectric layer.

19. The medical treatment device of claim 13, wherein the first planar electrode comprises a first part and a second part, wherein the first part is formed as a capacitive plate and is arranged with respect to the first dielectric material opposite to the second planar electrode, and wherein the second part is arranged with respect to the second dielectric material opposite to the inductive element, and wherein the first part and the second part are separated from each other and are electrically connected with each other by a connecting line.

20. The medical treatment device according to claim 13, wherein the first planar electrode and the inductive element are embedded at least partly in a soft magnetic ferrite material.

21. The medical treatment device according to claim 13, wherein the inductive sensor signal is obtained relative to a first reference potential and the capacitive sensor signal is obtained relative to a second reference potential.

22. A medical treatment device with a sensor for sensing operating states of a medical treatment device, the sensor comprising:

a first planar electrode arranged between a current path input and a current path output, the current path input is configured to couple to a power supply for powering the medical treatment device and the current path output is configured to couple to a load of the medical treatment device;

a second planar electrode for obtaining a capacitive sensor signal, the second planar electrode comprising a sense terminal to provide the capacitive sensor signal; and a dielectric material for separating the first planar electrode from the second planar electrode.

* * * * *